US009073802B2

(12) United States Patent
Takahashi et al.

(10) Patent No.: US 9,073,802 B2
(45) Date of Patent: Jul. 7, 2015

(54) METHOD FOR PRODUCING $^{18}$F-LABELED COMPOUND AND HIGH MOLECULAR COMPOUND TO BE USED IN THE METHOD

(75) Inventors: Takashi Takahashi, Tokyo (JP); Hiroshi Tanaka, Tokyo (JP); Tsutomu Nakada, Niigata (JP)

(73) Assignees: TOKYO INSTITUTE OF TECHNOLOGY, Tokyo (JP); NIIGATA UNIVERSITY, Niigata-shi (JP)

( * ) Notice: Subject to any disclaimer, the term of this patent is extended or adjusted under 35 U.S.C. 154(b) by 0 days.

(21) Appl. No.: 13/578,569

(22) PCT Filed: Feb. 8, 2011

(86) PCT No.: PCT/JP2011/052630
§ 371 (c)(1),
(2), (4) Date: Sep. 12, 2012

(87) PCT Pub. No.: WO2011/099480
PCT Pub. Date: Aug. 18, 2011

(65) Prior Publication Data
US 2012/0329968 A1 Dec. 27, 2012

(30) Foreign Application Priority Data
Feb. 12, 2010 (JP) ................................. 2010-029295

(51) Int. Cl.
*C07H 5/02* (2006.01)
*C08F 236/20* (2006.01)
(Continued)

(52) U.S. Cl.
CPC ............... *C07B 59/00* (2013.01); *C08F 236/20* (2013.01); *C07H 15/26* (2013.01); *A61K 51/0491* (2013.01)

USPC ........ 424/1.73; 424/1.11; 424/1.89; 526/335; 526/336

(58) Field of Classification Search
USPC .......................... 526/335, 336; 424/1.89, 1.73
See application file for complete search history.

(56) References Cited

U.S. PATENT DOCUMENTS

2007/0274911 A1* 11/2007 Brown et al. ................ 424/1.89
2009/0030192 A1 1/2009 Hirano et al.

FOREIGN PATENT DOCUMENTS

JP         2620109 B2 *  6/1997
JP      2005-512952 A    5/2005
(Continued)

OTHER PUBLICATIONS

Montanari, Fernando and Pietro Tundo, "Polymer-Supported Phase-Transfer Catalysts. Crown Ethers and Cryptands Bonded by a Long Alkyl Chain to a Polystyrene Matrix", 1981, Journal of Organic Chemistry, 46, 2125-2130.*
(Continued)

*Primary Examiner* — Ling Choi
*Assistant Examiner* — David L Miller
(74) *Attorney, Agent, or Firm* — Birch, Stewart, Kolasch & Birch, LLP

(57) ABSTRACT

The present invention aims at solving the problems of conventional methods for producing an $^{18}$F-labeled compound, that is, the problem of purification of a compound in a liquid phase synthesis method and the problem of an insufficient yield due to the reduction of reactivity in a solid phase synthesis method. There is provided a method for producing an $^{18}$F-labeled compound including: allowing a high molecular compound containing a residue of a precursor compound to be labeled and a residue of a phase transfer catalyst in the molecule thereof to react with $^{18}$F$^-$; and removing the $^{18}$F-labeled compound from the high molecular compound.

10 Claims, 1 Drawing Sheet

(51) Int. Cl.
*A61K 51/04* (2006.01)
*C07B 59/00* (2006.01)
*C07H 15/26* (2006.01)

(56) References Cited

FOREIGN PATENT DOCUMENTS

| | | | |
|---|---|---|---|
| JP | 2005-139341 A | | 6/2005 |
| JP | 2005139341 A | * | 6/2005 |
| JP | 2008-520636 A | | 6/2008 |
| WO | WO 03/002157 A1 | | 1/2003 |
| WO | WO 2004/056725 A1 | | 7/2004 |
| WO | WO 2005/012319 A1 | | 2/2005 |
| WO | WO 2006/054098 A2 | | 5/2006 |
| WO | WO 2007/063940 A1 | | 6/2007 |
| WO | WO 2007/066089 A2 | | 6/2007 |
| WO | WO 2009083530 A2 | * | 7/2009 |

OTHER PUBLICATIONS

International Preliminary Report or Patentability issued in corresponding international Application No. PCT/JP2011/052630 on Sep. 27, 2012.
PCT/ISA/210 of PCT/JP2011/052630 mailed on Mar. 8, 2011.
Office Action for Japanese Application No. 2011-553844, dated Dec. 2, 2014, with Partial English language translation.

* cited by examiner

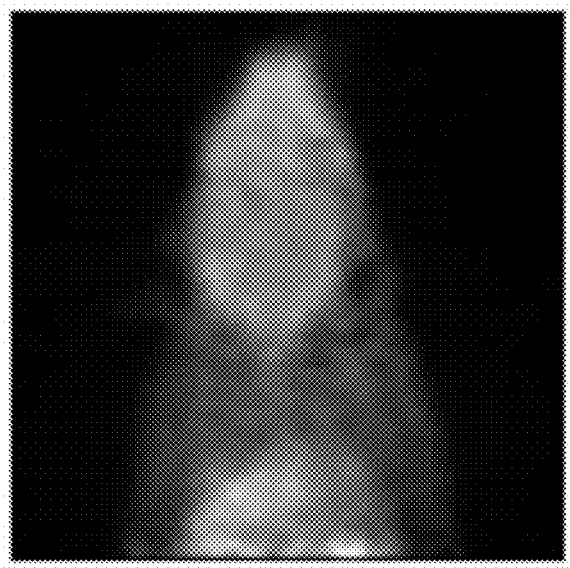

METHOD FOR PRODUCING ¹⁸F-LABELED COMPOUND AND HIGH MOLECULAR COMPOUND TO BE USED IN THE METHOD

TECHNICAL FIELD

The present invention relates to a method for producing an $^{18}$F-labeled compound and a high molecular compound to be used in the production method.

A quick and simple production method is required for the $^{18}$F nuclide because it has a half-life of only about 2 hours. The production method of the present invention allows quick and simple purification of an object because a precursor compound to be labeled immobilized in a high molecular compound is removed from the high molecular compound by the labeling with $^{18}$F. Furthermore, it is possible to produce the $^{18}$F-labeled compound more efficiently because the reactivity is improved by containing both the precursor compound to be labeled and a crown ether in the high molecular compound.

BACKGROUND ART

In the PET inspection used for the diagnosis of diseases such as cancer, $^{18}$F-labeled compounds are used as a probe. The $^{18}$F-labeled compounds are produced, for example, by the following liquid phase synthesis method, solid phase synthesis method, and the like.

Liquid phase synthesis method: A precursor compound to be labeled (a compound to be labeled) is allowed to react with a very small amount of $^{18}$F ions. As a result, a reaction product contains excess unreacted precursor compound to be labeled, thus requiring a very large amount of effort for the purification of an object compound. Furthermore, in order to overcome the low reactivity of fluoride ions, a highly reactive precursor compound to be labeled, that is, a low-stability precursor compound to be labeled is used in many cases.

Solid phase synthesis method: A precursor compound to be labeled immobilized on a solid phase is used, and only a reaction product is removed in a solution, thereby making the separation of the unreacted product and the reaction product easy (Patent Literature 1, Patent Literature 2, and Non Patent Literature 1). This method is expected to be an effective technique of facilitating the purification of a compound. However, a precursor compound to be labeled immobilized on a solid phase generally has a reduced reactivity. Furthermore, the immobilization on a solid phase reduces volume efficiency and increases the amount of solvent required, thus making it difficult to keep the concentration of fluoride ions at a high level. For this reason, although the purity of the compound obtained is high, it is difficult to obtain a sufficient amount of product. Such a problem of a solid phase synthesis method is pointed out also in Romain Bejot et al., Angew. Chem. Int. Ed. 2009, 48, pp. 586-589 (from the second line from the bottom of the left column to the third line of the right column on page 586).

CITATION LIST

Patent Literature

Patent Literature 1: National Publication of International Patent Application No. 2006-510706
Patent Literature 2: National Publication of International Patent Application No. 2007-500688

Non Patent Literature

Non Patent Literature 1: Lynda J. Brown et al., Angew. Chem. Int. Ed. 2007, 46, pp. 941-944

SUMMARY OF INVENTION

Technical Problem

An object of the present invention is to provide a means to solve the problems of conventional methods for producing an $^{18}$F-labeled compound, that is, the problem of purification of a compound in a liquid phase synthesis method and the problem of an insufficient yield due to the reduction of reactivity in a solid phase synthesis method.

Solution to Problem

In the solid phase synthesis method as described above, the immobilized precursor compound to be labeled and fluoride ions are allowed to react with each other in the presence of a crown ether (a phase transfer catalyst) (for example, Example 2 (vi) of Patent Literature 1 and Example 22 of Patent Literature 2). The present inventor has found that the reactivity of a precursor compound to be labeled with fluoride ions is significantly improved by immobilizing the crown ether on a high molecular compound together with the precursor compound to be labeled. The crown ether immobilized on a high molecular compound is generally predicted to have a lower reactivity as a catalyst than a crown ether in a free state. Consequently, it was not at all able to predict at the application of the present invention that immobilization of a crown ether on a high molecular compound improves the reactivity of a precursor compound to be labeled with fluoride ions.

The present invention has been completed based on the above findings.

Specifically, the present invention provides the following (1) to (10).

(1) A method for producing an $^{18}$F-labeled compound, comprising: allowing a high molecular compound containing a residue of a precursor compound to be labeled and a residue of a phase transfer catalyst in the molecule thereof to react with $^{18}$F⁻; and removing the $^{18}$F-labeled compound from the high molecular compound.

(2) The method for producing an $^{18}$F-labeled compound according to (1), wherein the high molecular compound is a high molecular compound obtained by copolymerization of a monomer containing a residue of a precursor compound to be labeled and a monomer containing a residue of a phase transfer catalyst.

(3) The method for producing an $^{18}$F-labeled compound according to (2), wherein the monomer containing a residue of a precursor compound to be labeled is a monomer represented by the following formula (I):

$$CH_2=C=CH-L^1-SO_2-X \quad (I)$$

wherein $L^1$ represents a linker, and X represents a residue of a precursor compound to be labeled; and the monomer containing a residue of a phase transfer catalyst is a monomer represented by the following formula (II):

$$CH_2=C=CH-L^2-Y \quad (II)$$

wherein $L^2$ represents a linker, and Y represents a residue of a phase transfer catalyst.

(4) The method for producing an $^{18}$F-labeled compound according to any one of (1) to (3), wherein the high molecular compound is a high molecular compound comprising structural units represented by the following formulas (Ia), (Ib), (IIa), and (IIb):

[Formula 1]

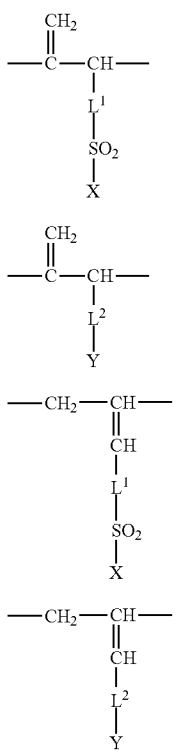

wherein $L^1$ and $L^2$ each represent a linker; X represents a residue of a precursor compound to be labeled; and Y represents a residue of a phase transfer catalyst.

(5) The method for producing an $^{18}$F-labeled compound according to any one of (1) to (4), wherein the phase transfer catalyst is Kryptofix [2,2,2], 12-crown-4, 15-crown-5, 18-crown-6, benzo-12-crown-4, benzo-15-crown-5, or benzo-18-crown-6.

(6) The method for producing an $^{18}$F-labeled compound according to any one of (1) to (5), wherein the precursor compound to be labeled is a compound represented by the following formula (A) or (B):

[Formula 2]

$R^1-CH_2-OH$ (A)

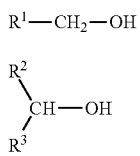 (B)

wherein $R^1$, $R^2$, and $R^3$ each represent any group.

(7) The method for producing an $^{18}$F-labeled compound according to any one of claims 1 to 6, wherein the $^{18}$F-labeled compound is 2-$^{18}$F-fluoro-2-deoxy-D-glucose, 2-$^{18}$F-fluoro-2-deoxy-D-mannose, 3-$^{18}$F-fluoro-3-deoxy-D-glucose, O-(2-[$^{18}$F]fluoroethyl)-L-tyrosine, 3'-[$^{18}$F]-fluoro-3'-deoxythymidine, 16α-[$^{18}$F]-fluoro-17β-estradiol, or [$^{18}$F]-fluoromisonidazole.

(8) A high molecular compound comprising structural units represented by the following formulas (Ia), (a), (IIa), and (IIb):

[Formula 3]

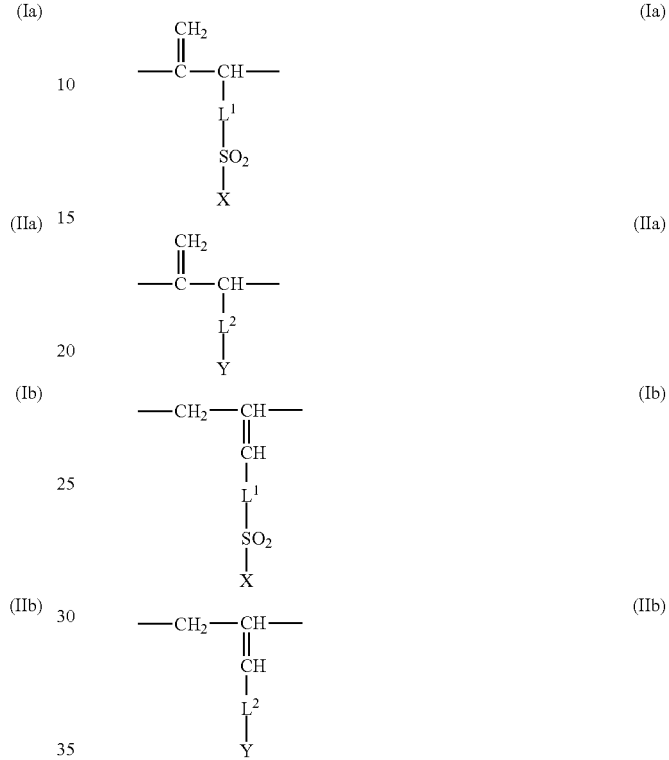

wherein $L^1$ and $L^2$ each represent a linker; X represents a residue of a precursor compound to be labeled; and Y represents a residue of a phase transfer catalyst.

(9) The high molecular compound according to (8), wherein the phase transfer catalyst is Kryptofix [2,2,2], 12-crown-4, 15-crown-5, 18-crown-6, benzo-12-crown-4, benzo-15-crown-5, or benzo-18-crown-6.

(10) The high molecular compound according to (8) or (9), wherein the precursor compound to be labeled is a compound represented by the following formula (A) or (B):

[Formula 4]

$R^1-CH_2-OH$ (A)

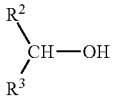 (B)

wherein $R^1$, $R^2$, and $R^3$ each represent any group.

Advantageous Effects of Invention

The present invention has, for example, the following effects.
1) A labeled compound is easily separated and purified from a precursor compound to be labeled and a phase transfer catalyst because only the labeled compound is removed from a high molecular compound.

2) The volume efficiency is about the same as in the case where a conventional precursor compound to be labeled soluble in a solvent is used because a high molecular compound is constructed from a precursor compound to be labeled and a phase transfer catalyst.

3) Reactivity is higher than in the case where the reaction is performed using a conventional precursor compound to be labeled soluble in a solvent. Therefore, it is possible to perform efficient fluorination using a precursor compound to be labeled which is more stable than conventional one.

BRIEF DESCRIPTION OF DRAWING

FIG. 1 is a PET image of the head of a mouse into which an [$^{18}$F]3-FDG solution is poured.

DESCRIPTION OF EMBODIMENTS

Hereinafter, the present invention will be described in detail.

The method for producing an $^{18}$F-labeled compound of the present invention comprises: allowing a high molecular compound containing a residue of a precursor compound to be labeled and a residue of a phase transfer catalyst in the molecule thereof to react with $^{18}$F$^-$; and removing the $^{18}$F-labeled compound from the high molecular compound.

An $^{18}$F-labeled compound as an object to be produced is not particularly limited, but since the $^{18}$F-labeled compound is mainly used as a probe for the diagnosis of diseases by PET, sugar, amino acid, and the like which are used as the probe for PET can be an object to be produced. Specifically, 2-$^{18}$F-fluoro-2-deoxy-D-glucose, 2-$^{18}$F-fluoro-2-deoxy-D-mannose, 3-$^{18}$F-fluoro-3-deoxy-D-glucose, O-(2-[$^{18}$F]fluoroethyl)-L-tyrosine, 3'-[$^{18}$F]-fluoro-3'-deoxythymidine, 16α-[$^{18}$F]-fluoro-17β-estradiol, [$^{18}$F]-fluoromisonidazole, and the like can be an object to be produced. Further, PET is used not only for the diagnosis of diseases but for knowing the pharmacokinetics of a drug, and therefore, such a drug may be an object to be produced. As described above, the method for producing an $^{18}$F-labeled compound of the present invention has a feature in that the labeled compound is easily purified, and this feature is suitable for the production of an $^{18}$F-labeled drug. This is because when a compound to be labeled with $^{18}$F is a compound which is present in a large amount in the body such as sugar and amino acid, a problem will hardly occur even if the labeled compound is administered in an unpurified state; however, when a compound to be labeled with $^{18}$F is a drug, a problem will occur that if the drug is administered in an unpurified state, an accurate pharmacokinetics of the drug cannot be grasped because an unlabeled compound will prevent the bonding or the like of the labeled compound.

A precursor compound to be labeled is not particularly limited as long as it is a compound removed from a high molecular compound in a form labeled with $^{18}$F by the reaction with $^{18}$F$^-$. A compound represented by the following (A) or (B) is present as a residue represented by the following (A-1) or (B-1) in a high molecular compound, and is removed from the high molecular compound as a compound represented by the following (A-2) or (B-2) by the reaction with $^{18}$F$^-$. Consequently, the compound represented by the following (A) or (B) can be used as a precursor compound to be labeled.

[Formula 5]

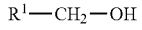  (A)

  (A-1)

  (A-2)

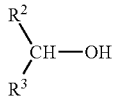  (B)

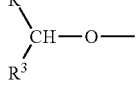  (B-1)

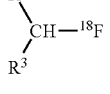  (B-2)

In the formulas, R$^1$, R$^2$, and R$^3$ each represent any group.

R$^1$, R$^2$, and R$^3$ each may be any group as described above, but if these groups contain a hydroxy group, $^{18}$F can be introduced into the hydroxy group. Consequently, when a hydroxy group is contained in R$^1$, R$^2$, and R$^3$, it is preferably protected by a suitable protective group.

Examples of suitable precursor compounds to be labeled include 1,3,4,6-tetra-O-acetyl-β-D-mannopyranose and 2-(trimethylsilyl)ethyl 4,6-isopropylidene-O-3-(ethoxyethyl)-mannoside which are labeling precursors of 2-$^{18}$F-fluoro-2-deoxy-D-glucose, 1,2,5,6-di-O-isopropylidene-α-D-allofuranose which is a labeling precursor of 3-$^{18}$F-fluoro-3-deoxy-D-glucose, 2-(trimethylsilyl)ethyl 4,6-ethylidene-3-O-(ethoxyethyl)-glucoside which is a precursor of 2-$^{18}$F-fluoro-2-deoxy-D-mannose, O-(2-hydroxyethyl)-N-trityl-L-tyrosine tert-butyl ester which is a precursor of O-(2-[$^{18}$F]fluoroethyl)-L-tyrosine, 3-N-Boc-5'-O -dimethyltrityl-thymidine which is a precursor of 3'-[$^{18}$F]-fluoro-3'-deoxythymidine, 3-O-methoxymethyl-16-O -(ethoxyethyl)-16-epiestriol which is a precursor of 16α-[$^{18}$F]-fluoro-17β-estradiol, and 1-(2'-nitro-1'-imidazoyl)-2-O-tetrahydropyranyloxy-1-propanol which is a precursor of [$^{18}$F]-fluoromisonidazole.

A phase transfer catalyst may be a compound which can catch a counter cation and can activate a counter anion $^{18}$F$^-$, and, for example, a crown ether can be used. Specific examples of crown ether include Kryptofix [2,2,2], 12-crown-4, 15-crown-5, 18-crown-6, benzo-12-crown-4, benzo-15-crown-5, and benzo-18-crown-6. A phase transfer catalyst to be used may be determined depending on the type of a counter cation of a fluoride ion used for reaction. For example, when the counter cation is a potassium ion, it is preferred to use Kryptofix [2,2,2], 18-crown-6, benzo-18-crown-6, and the like; and when the counter cation is a sodium ion, it is preferred to use 15-crown-5, benzo-15-crown-5, and the like.

The high molecular compound containing a residue of a precursor compound to be labeled and a residue of a phase transfer catalyst in the molecule thereof is obtained, for example, by copolymerization of a monomer containing a residue of a precursor compound to be labeled and a monomer containing a residue of a phase transfer catalyst.

The monomer containing a residue of a precursor compound to be labeled and the monomer containing a residue of a phase transfer catalyst are not particularly limited, but examples of the former include a monomer represented by the following formula (I) and examples of the latter include a monomer represented by the following formula (II).

(In the formula, $L^1$ represents a linker, and X represents a residue of a precursor compound to be labeled.)

(In the formula, $L^2$ represents a linker, and Y represents a residue of a phase transfer catalyst.)

A method for allowing the monomers represented by formulas (I) and (II) to copolymerize with each other to produce a high molecular compound is described in known literatures (for example, 1) Macromolecules 1994, 27, 4413. and 2) Taguchi, M.; Tomita, I.; Endo, T., Angew. Chem. Int. Ed. 2000, 39, 3667.), and a person skilled in the art will be able to easily produce the target high molecular compound from these literatures.

The high molecular compound obtained by copolymerization of monomers represented by formula (I) and formula (II) comprises structural units represented by the following formulas (Ia), (Ib), (IIa), and (IIb):

[Formula 6]

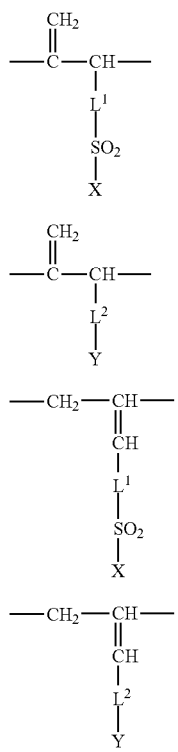

wherein $L^1$ and $L^2$ each represent a linker; X represents a residue of a precursor compound to be labeled; and Y represents a residue of a phase transfer catalyst.

$L^1$ and $L^2$ in the above formulas are not particularly limited as long as they are linkers which can hold the distance between the main chain of a high molecular compound and a reactive site. Specific examples include linkers which consist of one or more groups selected from the group consisting of 0 to 4 aryl groups (suitably phenyl), an alkyl group having 1 to 6 carbon atoms, a fluoroalkyl group having 1 to 6 carbon atoms, an alkoxy group having 1 to 6 carbon atoms, and a fluoroalkoxy group having 1 to 6 carbon atoms and suitably contain 1 to 4 functional groups such as a sulfonyl group, an amide group, or a sulfonamide group. Furthermore, these linkers are described in known literatures (for example, National Publication of International Patent Application No. 2006-510706 and National Publication of International Patent Application No. 2007-500688), and a person skilled in the art can select a suitable linker based on these literatures.

Examples of suitable $L^1$ and $L^2$ include, but are not limited to, linkers represented by the following formula (III) and (IV), respectively:

[Formula 7]

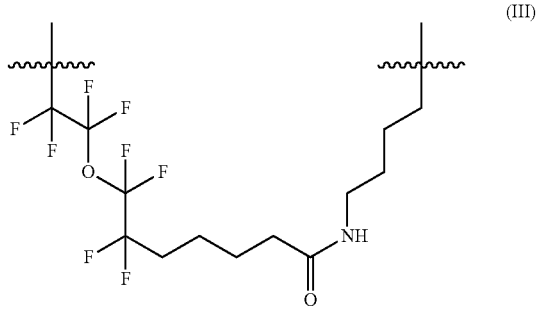

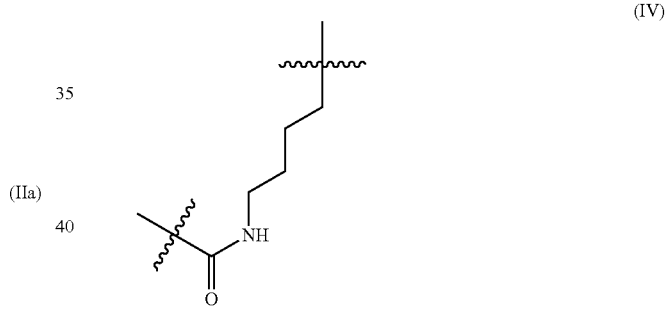

When only the monomers represented by formula (I) and (II) are copolymerized, a linear high molecular compound will be produced, but the high molecular compound may be a network high molecular compound by adding a different structural unit to these structural units and producing crosslinking. Examples of the different structural unit for forming the network high molecular compound include a structural unit represented by the following formula (V):

[Formula 8]

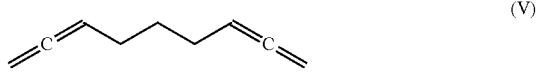

It is predicted that the solubility of the high molecular compound in a solvent is reduced by converting the high molecular compound into a network state from a linear state. This will facilitate the isolation of the removed $^{18}$F-labeled compound.

A functional group may be added to the high molecular compound in order to facilitate the separation thereof from a solvent or the like. Examples of the functional group to be added include a long chain alkyl group and a perfluoroalkyl group.

Further, the high molecular compound may be supported by a solid phase insoluble in a solvent. Thereby, the isolation of the removed $^{18}$F-labeled compound will probably be easier.

The molecular weight of the high molecular compound is, but not particularly limited to, preferably 500 to 50,000,000, more preferably 5,000 to 5,000,000, further preferably 50,000 to 500,000.

The number of the residue of the precursor compound to be labeled contained in the high molecular compound is, but not particularly limited to, preferably 50 to 50,000, more preferably 50 to 5,000, further preferably 50 to 500.

The number of the residue of the phase transfer catalyst contained in the high molecular compound is, but not limited to, preferably 50 to 50,000, more preferably 50 to 5,000, further preferably 50 to 500.

The ratio of the number of the residue of the precursor compound to be labeled to the number of the residue of the phase transfer catalyst in the high molecular compound is not particularly limited, but the ratio of the former to the latter is preferably 1000:1 to 1:1000, more preferably 100:1 to 1:100, further preferably 10:1 to 10:1.

The reaction of the high molecular compound and $^{18}$F$^-$ can be performed by allowing the high molecular compound and a salt containing fluoride ions to be present together in a suitable solvent. Examples of the salt containing fluoride ions include LiF, KF, NaF, and CsF. Examples of the solvent include acetonitrile, propionitrile, dimethylformamide, dimethyl sulfoxide, ethanol, butanol, dioxane, water, and a mixed solvent thereof. The concentration of the high molecular compound in a solvent is, but not particularly limited to, preferably 0.1 to 1000 mg/mL, more preferably 1 to 100 mg/mL, further preferably 10 to 100 mg/mL. The concentration of the salt containing fluoride ions in a solvent is also not particularly limited, but it is preferably 1 pM to 1 M, more preferably 100 pM to 1 mM, further preferably 1 pM to 1 µM.

The temperature during the reaction of the high molecular compound with $^{18}$F$^-$ is, but not particularly limited to, preferably 0 to 200° C., more preferably 50 to 150° C., further preferably 80 to 100° C.

The time required for the reaction of the high molecular compound with $^{18}$F$^-$ is, but not particularly limited to, preferably 0.1 to 30 minutes, more preferably 1 to 15 minutes, further preferably 5 to 10 minutes.

Purification of the $^{18}$F-labeled compound from the reaction product can be performed in accordance with conventional methods, such as chromatography and filtration. The purified $^{18}$F-labeled compound can optionally be subjected to deprotection or the like to produce an object compound.

EXAMPLES

The present invention will be described in further detail below with reference to Examples.

Example 1

Production of 3-FDG

Example 1-1

Synthesis of 1,2,5,6-di-O-isopropylidene-α-D-allofuranose

[Formula 9]

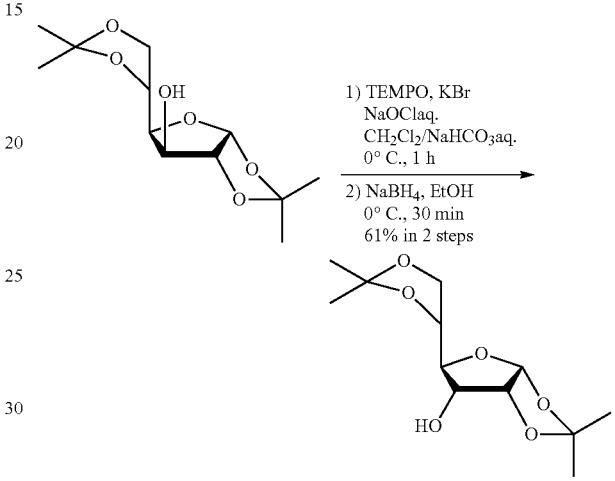

To a solution of 1,2,5,6-di-O-isopropylidene-α-D -glucofuranose (5.02 g, 19.2 mmol, 1.00 eq.) in a mixture of dry methylene chloride (30.0 mL) and saturated sodium bicarbonate water (3.00 mL), were added a catalytic amount of TEMPO, KBr, and an aqueous NaOCl solution (30.0 mL) at 0° C. The mixture was allowed to react at the same temperature for 1 hour and then the resulting reaction solution was poured into 1 N hydrochloric acid with ice-cooling. The aqueous phase was extracted twice with ethyl acetate, and then the organic phase was washed with 1 N hydrochloric acid, saturated sodium bicarbonate water, and a saturated salt solution, and finally dried over magnesium sulfate. The solvent was removed under reduced pressure to obtain a crude product. The obtained crude product was used for the next reaction as it is.

To a solution (30.0 mL) of the crude product in ethanol, was gradually added sodium borohydride (1.09 g, 28.8 mmol, 1.50 eq.) with ice-cooling. The mixture was stirred for 30 minutes at room temperature, and then the reaction solution was poured into a saturated aqueous ammonium chloride solution. The aqueous phase was extracted twice with ethyl acetate, and then the organic phase was washed with a saturated aqueous ammonium chloride solution, saturated sodium bicarbonate water, and a saturated salt solution, and finally dried over magnesium sulfate. The solvent was removed under reduced pressure to obtain a crude product. The obtained crude product was purified by silica gel column chromatography (eluent: hexane:ethyl acetate=6:4) to obtain 1,2,5,6-di -O-isopropylidene-α-D-allofuranose as shown below (3.05 g, 11.7 mmol, 61% in 2 steps).

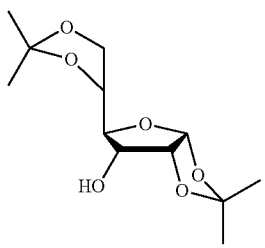

Furthermore, the analysis results of the obtained compound were as follows.

$[\alpha]_D^{26}$ 39.3° (c=1.05, CHCl$_3$); $^1$H NMR (400 MHz, CDCl$_3$) δ 5.83 (d, 1H, H-1, $J_{1,2}$=3.9 Hz), 4.62 (dd, 1H, H-2, $J_{1,2}$=3.9 Hz, $J_{2,3}$=5.3 Hz), 4.31 (ddd, 1H, H-3, $J_{2,3}$=5.3 Hz, $J_{3,4}$=8.7 Hz, $J_{3,OH}$=8.2 Hz), 4.00-4.11 (m, 3H, H-4, H-5, H-6a), 3.82 (dd, 1H, H-6b, $J_{5,6b}$=4.8 Hz, $J_{6a,6b}$=9.2 Hz), 2.58 (d, 1H, OH, $J_{3,OH}$=8.2 Hz), 1.58 (s, 3H, Me), 1.47 (s, 3H, Me), 1.39 (s, 3H, Me), 1.38 (s, 3H, Me); $^{13}$C NMR (100 MHz, CDCl$_3$) δ (112.6, 109.7 isopropylidene), (103.7 anomeric), 79.5, 78.9, 75.4, 72.3, 65.6, 26.4, 26.1, 25.1; FT-IR (neat) 3483, 1375, 1216, 1061, 870 (cm$^{-1}$); HRMS (ESI-TOF) Calcd for [M+Na]$^+$, found

Example 1-2

Synthesis of 1,2,5,6-di-O-isopropylidene-3-O-(5-iodooctafluoro-3-oxapentanesulfonyl)-α-D-allofuranose

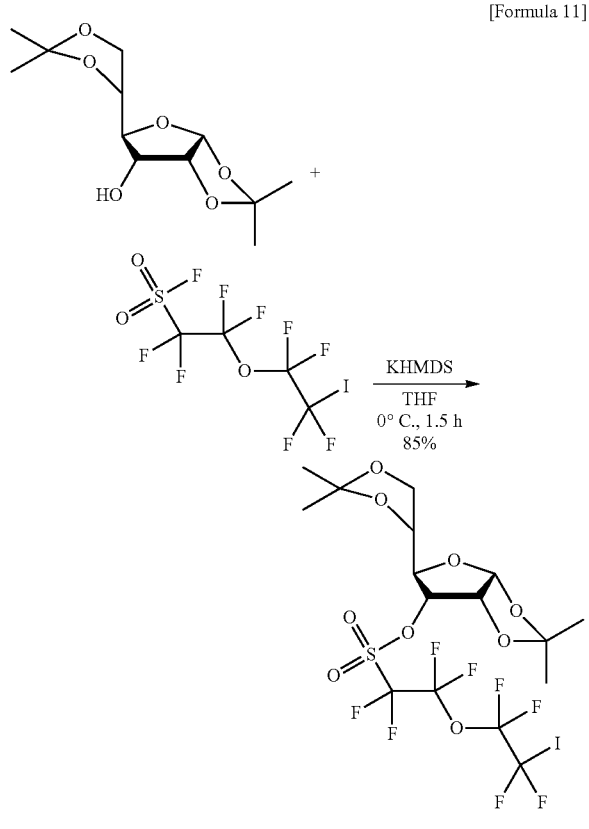

To a solution of 1,2,5,6-di-O-isopropylidene-α-D-allofuranose (781 mg, 3.00 mmol, 1.00 eq.) in dry THF (10.0 mL), was added KHMDS (0.5 M THF solution, 6.80 mL, 3.60 mmol, 1.20 eq.) with ice-cooling in an argon atmosphere, and the mixture was stirred at the same temperature for 30 minutes. To the resulting solution was dropwise added 5-iodooctafluoro-3-oxapentanesulfonyl fluoride (1.40 g, 3.30 mmol, 1.10 eq.) over 30 minutes. The mixture was stirred for further 15 minutes at the same temperature, and then the reaction solution was poured into saturated sodium bicarbonate water. The aqueous phase was extracted twice with ethyl acetate, and then the organic phase was washed with saturated sodium bicarbonate water and a saturated salt solution, and finally dried over magnesium sulfate. The solvent was removed under reduced pressure to obtain a crude product. The obtained crude product was purified by silica gel column chromatography (eluent: hexane:ethyl acetate=92:8) to obtain 1,2,5,6-di-O-isopropylidene-3-O-(5-iodooctafluoro-3-oxapentanesulfonyl)-α-D-allofuranose as shown below (1.70 g, 2.55 mmol, 85%).

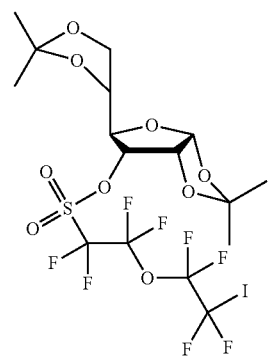

Example 1-3

Synthesis of 1,2,5,6-di-O-isopropylidene-3-O-(9-carbonyl-3-oxa-1,1,2,2,4,4,5,5-octafluoro-7-iodo-6-nonenesulfonyl)-α-D-allofuranose

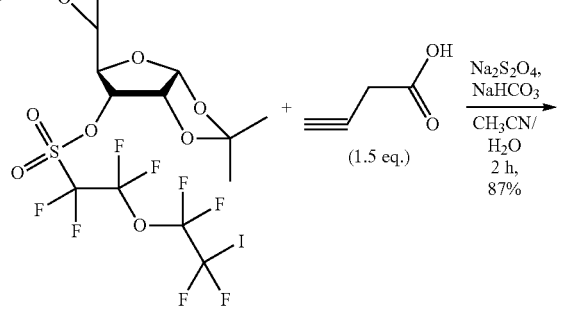

-continued

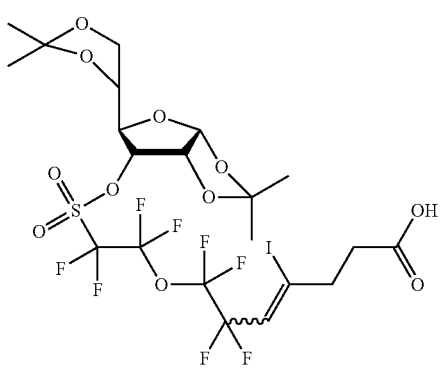

To a solution of 1,2,5,6-di-O-isopropylidene-3-O-(5-iodooctafluoro-3-oxapentanesulfonyl)-α-D-allofuranose (1.58 g, 2.37 mmol, 1.00 eq.) and 4-pentynoic acid (349 mg, 3.56 mmol, 1.50 eq.) in a mixture of acetonitrile (12.0 mL) and water (12.0 mL), were added $Na_2S_2O_4$ (619 mg, 3.56 mmol, 1.50 eq.) and $NaHCO_3$ (299 mg, 3.56 mmol, 1.50 eq.) at room temperature. The mixture was allowed to react at room temperature for 2 hours, and then the resulting reaction solution was poured into water. The aqueous phase was extracted twice with ethyl acetate, and then the organic phase was washed with saturated sodium bicarbonate water and a saturated salt solution, and finally dried over magnesium sulfate. The solvent was removed under reduced pressure to obtain a crude product. The obtained crude product was purified by silica gel column chromatography (eluent: chloroform:methanol=99:1) to obtain 1,2,5,6-di-O-isopropylidene-3-O-(9-carbonyl-3-oxa-1,1,2,2,4,4,5,5-octafluoro-7-iodo-6-nonenesulfonyl) -α-D-allofuranose as shown below (1.55 g, 2.03 mmol, 87%).

[Formula 14]

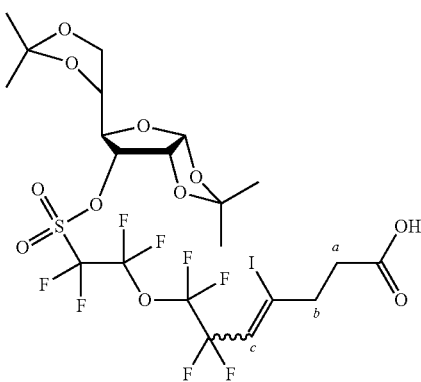

Example 1-4

Synthesis of 1,2,5,6-di-O-isopropylidene-3-O-(9-carbonyl-3-oxa-1,1,2,2,4,4,5,5-octafluorononenanesulfonyl)-α-D-allofuranose

[Formula 15]

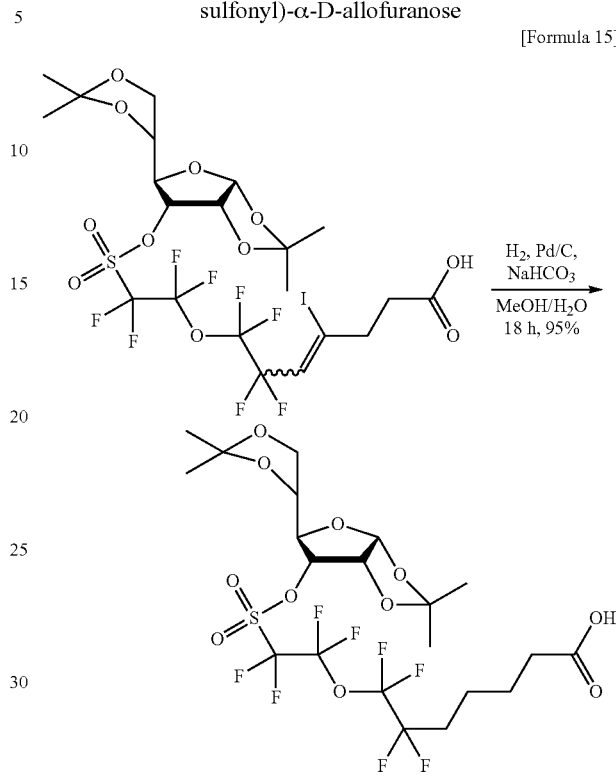

To a solution of 1,2,5,6-di-O-isopropylidene-3-O-(9-carbonyl-3-oxa-1,1,2,2,4,4,5,5-octafluoro-7-iodo-6-nonenesulfonyl)-α-D-allofuranose (221 mg, 289 μmol, 1.00 eq.) in a mixture of methanol (1.40 mL) and water (1.40 mL), were added saturated sodium bicarbonate water (72.8 mg, 867 μmol, 3.00 eq.) and Pd/C (110 mg). The resulting solution was stirred in a hydrogen atmosphere for 18 hours. Then, the reaction solution was filtered, and the filtrate was poured into water. The aqueous phase was extracted twice with ethyl acetate, and then the organic phase was washed with saturated sodium bicarbonate water and a saturated salt solution, and finally dried over magnesium sulfate. The solvent was removed under reduced pressure to obtain a crude product. The obtained crude product was purified by silica gel column chromatography (eluent: chloroform:methanol=99:1) to obtain 1,2,5,6-di -O-isopropylidene-3-O-(9-carbonyl-3-oxa-1,1,2,2,4,4,5,5-octafluorononenanesulfonyl)-α-D-allofuranose as shown below (175 mg, 273 μmol, 95%).

[Formula 16]

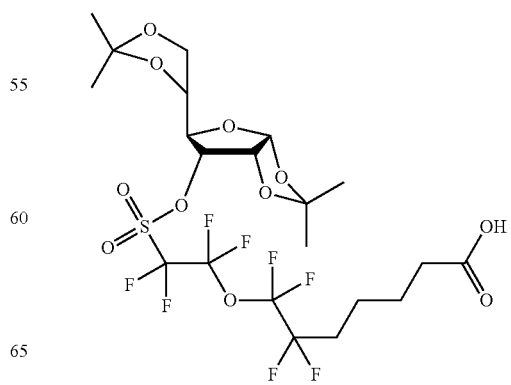

Example 1-5

Synthesis of N-(5,6-heptadiene)phthalimide

[Formula 17]

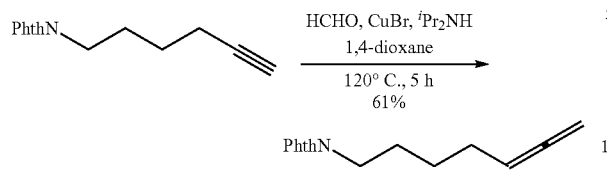

To a solution of N-(5-hexyne)naphthalimide (7.10 g, 31.2 mmol, 1.00 eq.) in 1,4-dioxane (62.0 mL), were added paraformaldehyde (1.88 g, 62.5 mmol, 2.00 eq.), copper bromide (1.57 g, 10.9 mmol, 0.350 eq.), and diisopropylamine (8.82 mL, 62.5 mmol, 2.00 eq.), and they were allowed to react with each other at 120° C. for 5 hours. Then, the reaction solution was filtered, and the filtrate was poured into water. The aqueous phase was extracted twice with ethyl acetate, and then the organic phase was washed with 1 N aqueous hydrochloric acid solution, saturated sodium bicarbonate water, and a saturated salt solution, and finally dried over magnesium sulfate. The solvent was removed under reduced pressure to obtain a crude product. The obtained crude product was purified by silica gel column chromatography (eluent: hexane:ethyl acetate=90:10) to obtain N-(5,6-heptadiene)phthalimide as shown below (4.65 g, 19.3 mmol, 61%).

[Formula 18]

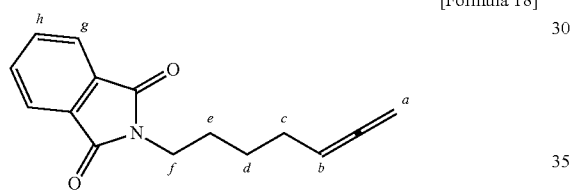

Example 1-6

Synthesis of 1-amino-5,6-heptadiene

[Formula 19]

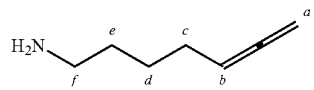

To a solution of N-(5,6-heptadiene)phthalimide (4.65 g, 19.3 mmol, 1.00 eq.) in methanol (40.0 mL), was added $H_2NNH_2 \cdot H_2O$ (1.93 mL, 38.5 mmol, 2.00 eq.), and they were allowed to react with each other at 70° C. for 2 hours. Subsequently, the reaction system was converted to an alkaline form with an aqueous concentrated sodium hydroxide solution and then extracted with methylene chloride to thereby obtain an object, 1-amino-5,6-heptadiene as shown below (1.81 g, 16.3 mmol, crude yield 85%).

[Formula 20]

Example 1-7

Synthesis of Sugar Allene Monomer

[Formula 21]

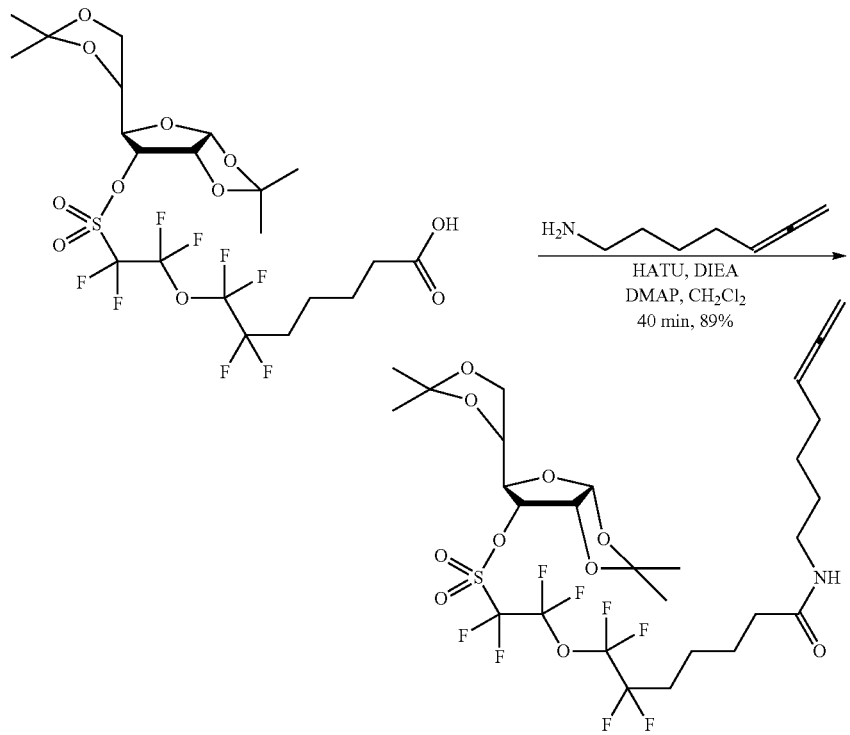

To a solution of 1,2,5,6-di-O-isopropylidene-3-O-(9-carbonyl-3-oxa-1,1,2,2,4,4,5,5-octafluorononenanesulfonyl)-α-D-allofuranose (674 mg, 1.05 mmol, 1.00 eq.) and 1-amino-5,6-heptadiene (351 mg, 3.16 mmol, 3.00 eq.) in a dry methylene chloride solvent (1.00 mL), were added HATU (600 mg, 1.58 mmol, 1.50 eq.), diisopropylethylamine (272 µL, 1.58 mmol, 1.50 eq.), and a catalytic amount of N,N-dimethylamino pyridine at room temperature. The mixture was stirred at room temperature for 40 minutes, and the reaction solution was filtered. The resulting filtrate was concentrated, and the resulting residue was purified by silica gel column chromatography (eluent: hexane:ethyl acetate=80:20) to obtain a sugar allene monomer as shown below (685 mg, 0.934 mmol, 89%).

To a solution of 4-carboxybenzo-18-crown-6 (32.3 mg, 90.6 µmol, 1.00 eq.) and 1-amino-5,6-heptadiene (30.2 mg, 272 µmol, 3.00 eq.) in a dry methylene chloride solvent (1.00 mL), were added HATU (51.7 mg, 136 µmol, 1.50 eq.), diisopropylethylamine (23.4 µL, 136 µmol, 1.50 eq.), and a catalytic amount of N,N-dimethylaminopyridine at room temperature. The mixture is stirred at room temperature for 40 minutes, and the reaction solution is filtered. The resulting filtrate was concentrated, and the resulting residue was purified by silica gel column chromatography (eluent: chloroform:methanol=95:5) to obtain a crown ether allene monomer as shown below (39.3 mg, 64.3 µmol, 71%).

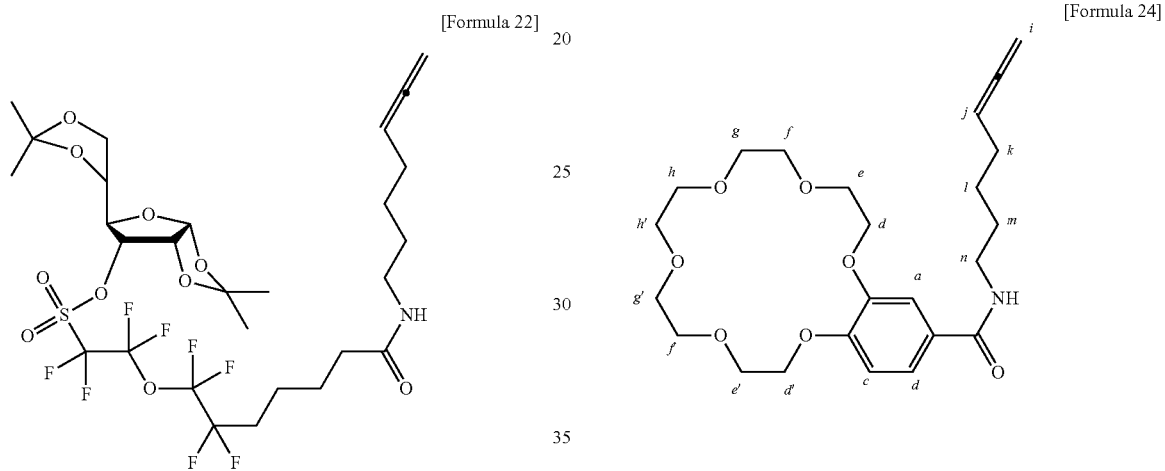

[Formula 22]

Example 1-8

Synthesis of Crown Ether Allene Monomer

[Formula 24]

Example 1-9

Synthesis of Copolymer

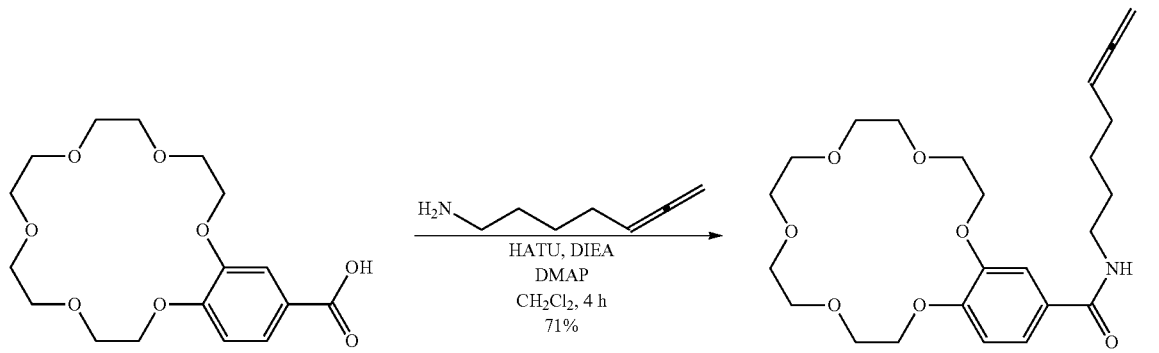

[Formula 23]

[Formula 25]
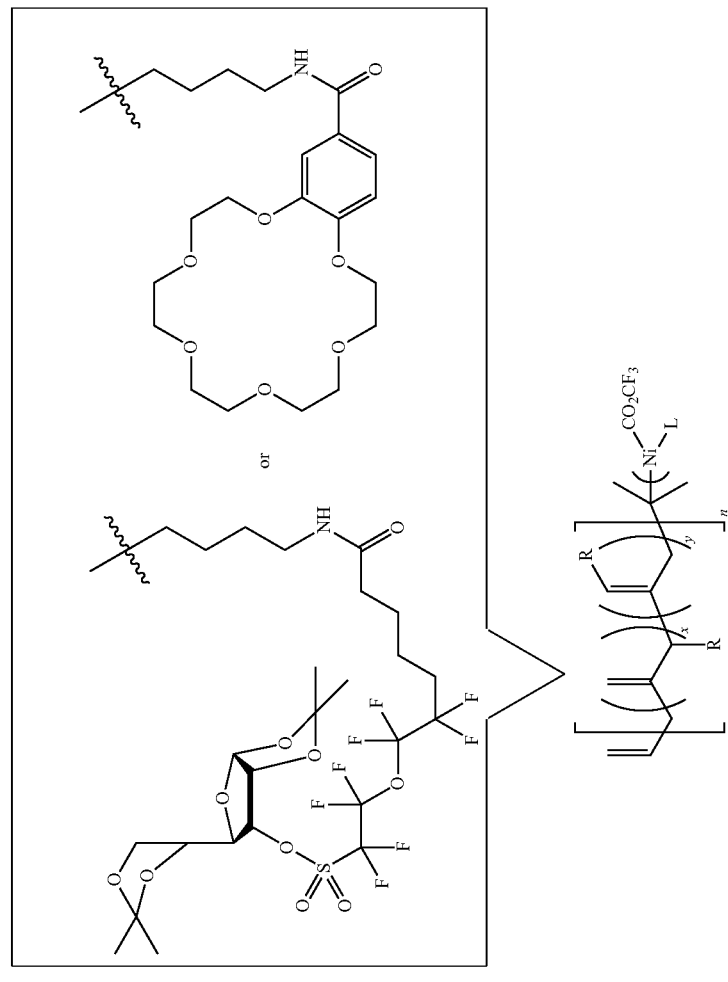
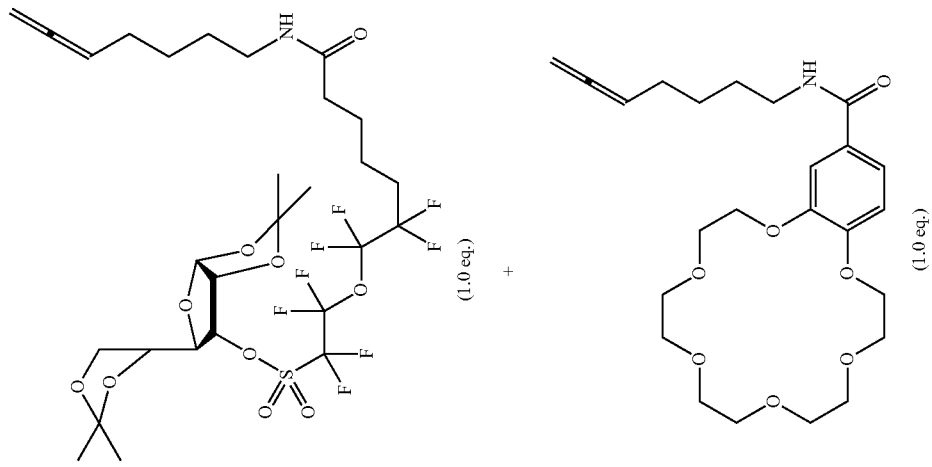

To a mixed solution of a toluene solution of 0.10 M bis(1,5-cyclooctadiene)nickel (73.5 μL, 0.735 μmol, 0.0500 eq.) and a toluene solution of 1.0 M allyl trifluoroacetate (11.8 μL, 1.18 μmol, 0.0800 eq.), were added a sugar allene monomer (108 mg, 14.7 μmol, 1.00 eq.) and a crown ether allene monomer (66.0 mg, 14.7 μmol, 1.00 eq.) which were dissolved in a methanol solution (0.500 mL) in a nitrogen atmosphere. The mixture was allowed to react for 7 days, and then the resulting reaction solution was diluted with hexane to allow a purified product to be precipitated. The resulting precipitate was filtered to thereby obtain the target copolymer (154 mg, 13.0 μmol, 89%).

Example 1-10

Fluorine Addition Reaction (1)

[Formula 26]
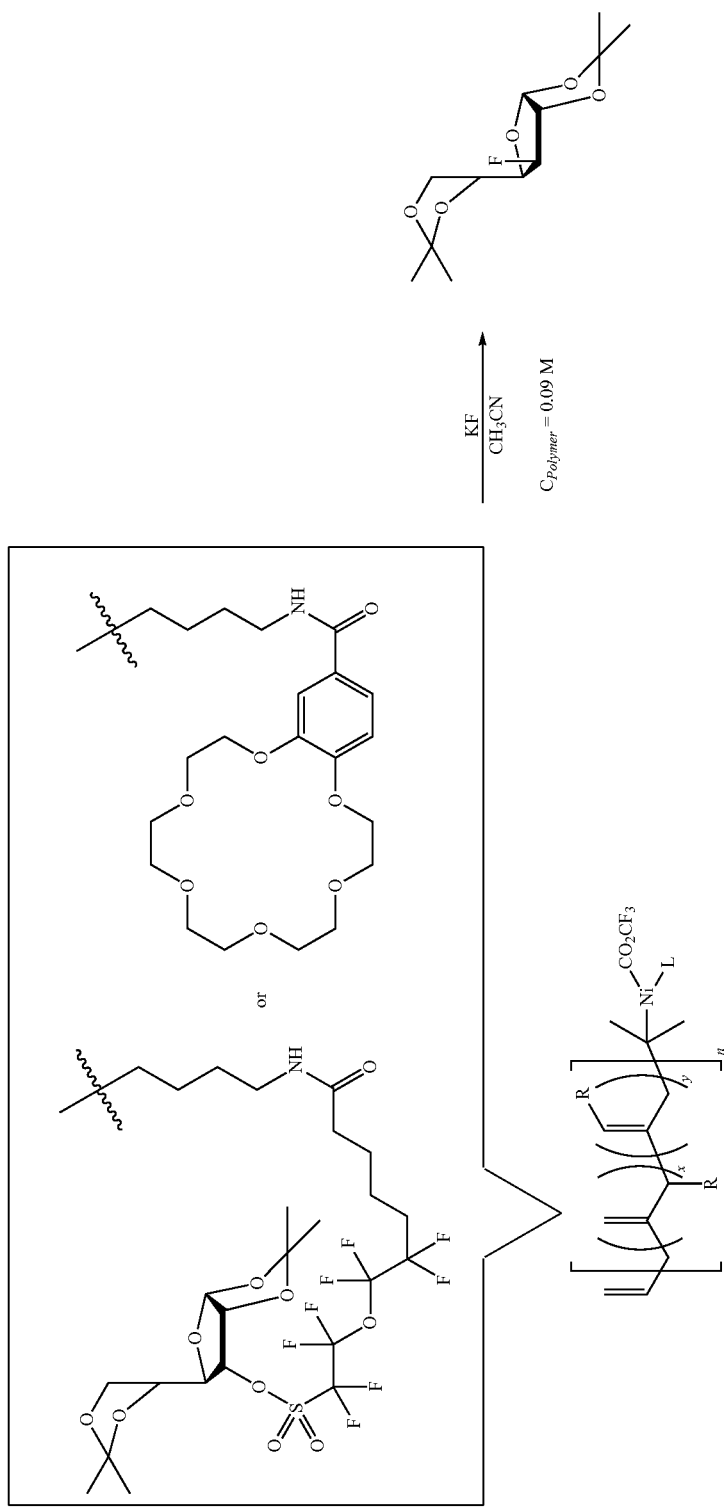

A copolymer was subjected to fluorine addition reaction by adding KF so that KF might be 5.0 equivalents to the copolymer.

The copolymer (10.6 mg, 9.39 μmol, 1.00 eq.) synthesized in Example 9 was dissolved in acetonitrile (100 μL). To the solution was added KF (2.73 mg, 47.0 μmol, 5.00 eq.). The resulting solution was allowed to react at 95° C. for 30 minutes. The reaction solution was concentrated and then purified by silica gel column chromatography to obtain 3-deoxy-3-fluoro-1,2,5,6-di-O-isopropylidene-α-D-glucofuranose (1.20 mg, 4.58 μmol). The yield was 58%.

Example 1-11

Fluorine Addition Reaction (2)

A copolymer was subjected to fluorine addition reaction by adding KF so that KF might be 1.0 equivalent to the copolymer.

The copolymer (24.3 mg, 21.3 μmol, 1.00 eq.) synthesized in Example 9 was dissolved in acetonitrile (200 μL). To the solution was added KF (1.23 mg, 21.3 μmol, 1.00 eq.). The resulting solution was allowed to react at 95° C. for 30 minutes. The reaction solution was concentrated and then purified by silica gel column chromatography to obtain 3-deoxy-3-fluoro-1,2,5,6-di-O-isopropylidene-α-D-glucofuranose (1.70 mg, 8.09 μmol). The yield was 38%.

Example 1-12

Fluorine Addition Reaction (3)

A copolymer was subjected to fluorine addition reaction by adding KF so that KF might be 0.5 equivalent to the copolymer.

The copolymer (30.5 mg, 25.1 μmol, 2.00 eq.) synthesized in Example 9 was dissolved in acetonitrile (250 μL). To the solution was added KF (0.730 mg, 12.5 μmol, 1.00 eq.). The resulting solution was allowed to react at 95° C. for 30 minutes. The reaction solution was concentrated and then purified by silica gel column chromatography to obtain 3-deoxy-3-fluoro-1,2,5,6-di-O-isopropylidene-α-D-glucofuranose (1.50 mg, 5.78 mmol). The yield was 46%.

Example 1-13

Fluorine Addition Reaction (4)

The copolymer (17.1 mg, 14.5 μmol, 1.00 eq.) synthesized in Example 9 was dissolved in acetonitrile (235 μL). To the solution was added KF (2.30 mg, 39.2 μmol, 2.70 eq.). The resulting solution was allowed to react at room temperature for 6 hours. The reaction solution was concentrated and then purified by silica gel column chromatography to obtain 3-deoxy-3-fluoro-1,2,5,6-di-O-isopropylidene-α-D-glucofuranose (1.60 mg, 6.10 μmol). The yield was 44%.

Comparative Example

Fluorine Addition Reaction (5)

[Formula 27]

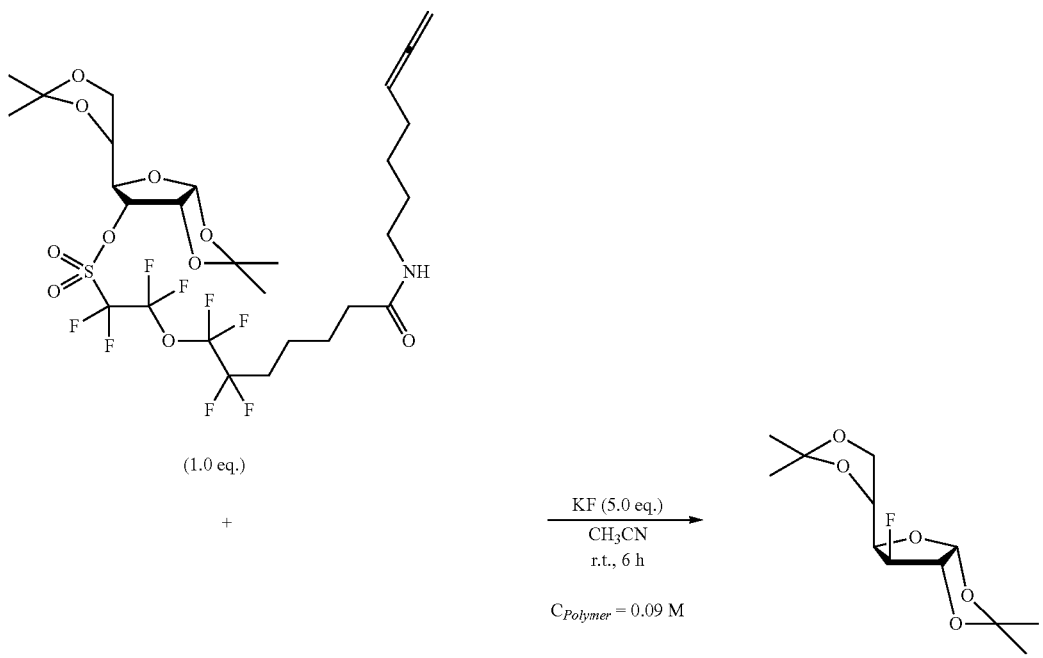

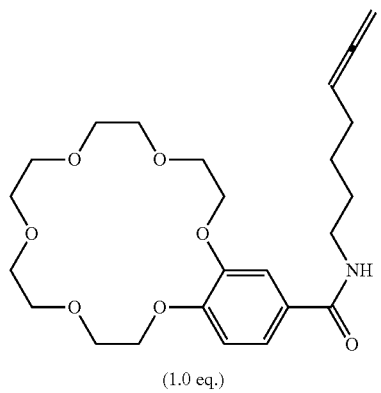

(1.0 eq.)

A sugar allene monomer and a crown ether allene monomer were subjected to fluorine addition reaction, and the results were compared with the result of fluorine addition reaction to the copolymer.

The sugar allene monomer (40.3 mg, 55.0 μmol, 1.00 eq.) synthesized in Example 7 and the crown ether allene monomer (24.7 mg, 55.0 μmol, 1.00 eq.) synthesized in Example 8 were dissolved in acetonitrile (600 μL). To the solution was added KF (2.30 mg, 39.2 μmol, 2.70 eq.). The resulting solution was allowed to react at room temperature for 6 hours. The reaction solution was concentrated and then purified by silica gel column chromatography to obtain 3-deoxy-3-fluoro-1,2,5,6-di-O-isopropylidene-α-D-glucofuranose (0.8 mg, 3.1 μmol). The yield was 5%.

Example 1-14

Synthesis of [$^{18}$F]3-FDG

[$^{18}$F]3-FDG was synthesized as follows using a PET tracer synthesizer manufactured by GE Company. $^{18}$F-ions were synthesized using a cyclotron and immobilized in a Chromafix column. A potassium carbonate solution (3.0 mg/0.5 ml) was poured to obtain an aqueous [$^{18}$F]KF solution (5 GBq) in the reaction vessel. A solution (1.0 mL) of the copolymer (40 mg) synthesized in Example 9 in acetonitrile was put into the reaction vessel and maintained at 55 degrees for 2.5 minutes and at 85 degrees for 3 minutes, and finally concentrated to dryness at 60 degrees. Subsequently, thereto was added acetonitrile (1.0 mL), and the resulting mixture was heated at 85 degrees for 5 minutes. The heated mixture was once cooled to 50 degrees, and then maintained at 55 degrees for 50 seconds and at 105 degrees for 50 seconds, and finally brought to 90 degrees to thereby remove the solvent. To the resulting mixture was added 1 M aqueous hydrochloric acid solution (2 ml) and heated at 125 degrees for 15 minutes. The heated mixture was cooled to 50 degrees, and thereto was added 7% aqueous sodium bicarbonate solution (4.5 mL). The mixture was purified by passing through a Chromabond V column and finally passing through a membrane filter (Milipore) to thereby obtain the target [$^{18}$F]3-FDG (1.2 GBq). A one-third solution of the obtained [$^{18}$F]3-FDG (1.2 GBq) was injected into a mouse, and the behavior was observed. As a result, it was verified that the target [$^{18}$F]3-FDG had been synthesized based on the verification of its invasion into the brain (FIG. 1).

Example 2

Production of 2-FDG

Example 2-1

Synthesis of 2-FDG Monomer

The synthesis steps of 2-FDG monomer are shown below.

[Formula 28]

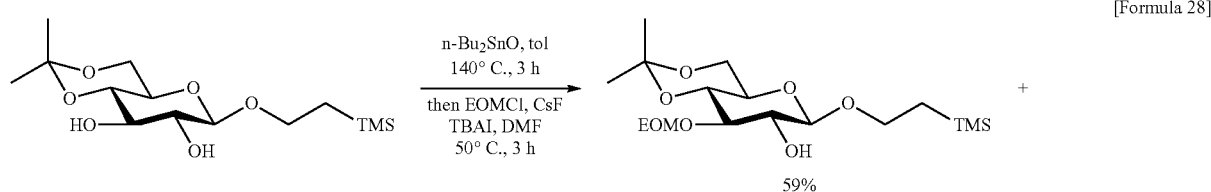

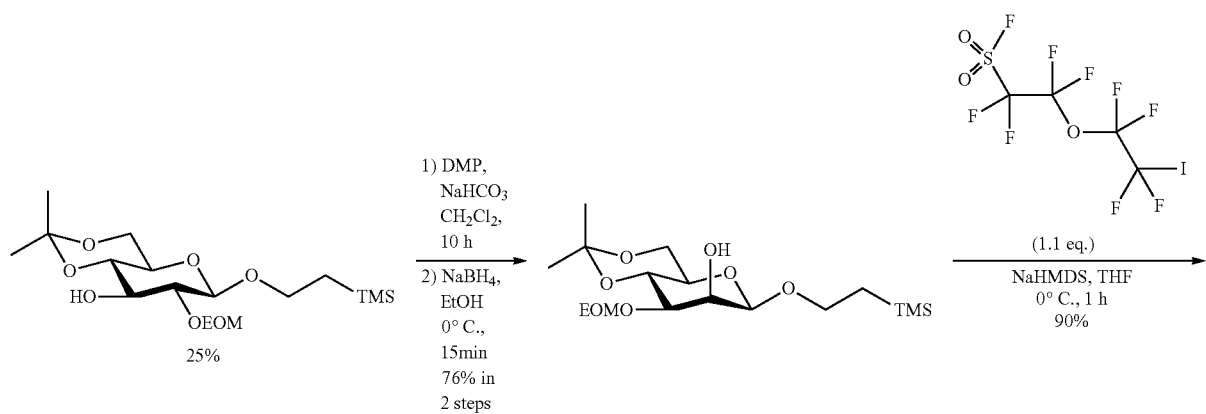
[Formula 29]
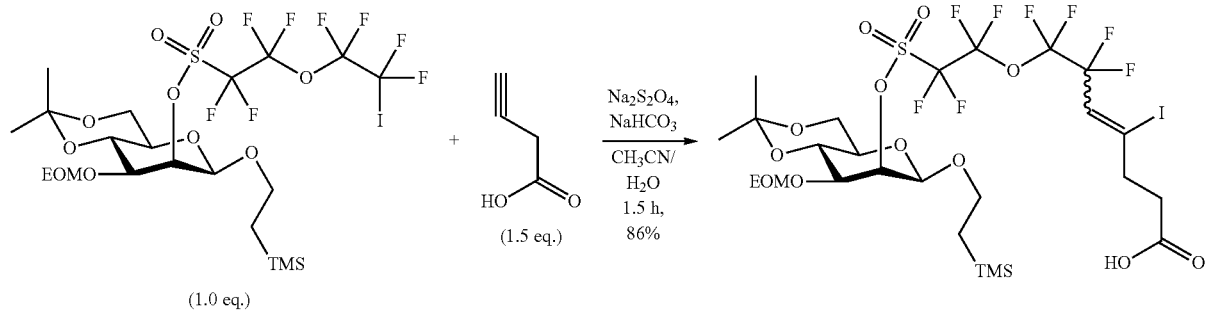
[Formula 30]
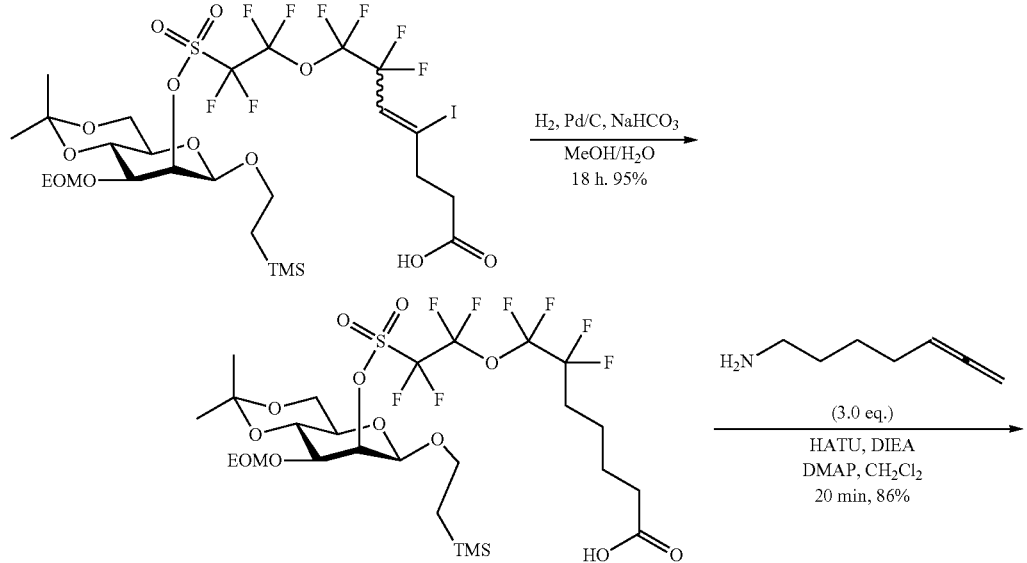

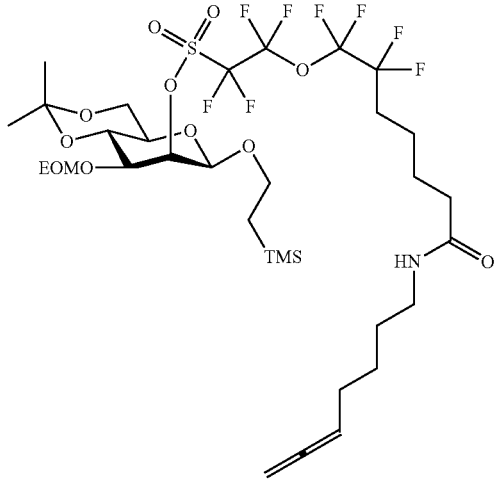

Example 2-1-1

Synthesis of 2-trimethylsilylethyl 3-O-ethoxymethyl-4,6-isopylidene-β-D-glucopyranoside To a solution of 2-trimethylsilylethyl 4,6-isopylidene-β-D-glucopyranoside (1.51 g, 4.71 mmol, 1.00 eq.) in dry toluene (20.0 mL), was added dibutyltin oxide (1.41 g, 5.66 mmol, 1.20 eq.) at room temperature. The mixture was allowed to react at 140 degrees for 3 hours, and then the solvent was removed under reduced pressure. The obtained residue was azeotropically concentrated with the dry toluene, and then thereto were added ethoxymethyl chloride (630 μL, 6.13 mmol, 1.30 eq.) and cesium fluoride (1.43 g, 9.42 mmol, 2.00 eq.). The mixture was allowed to react at 50 degrees for 3 hours and then poured into 1 M aqueous hydrochloric acid solution with ice-cooling. The resulting aqueous phase was extracted with ethyl acetate, and then the organic phase was washed with 1 M aqueous hydrochloric acid solution, a saturated aqueous sodium bicarbonate solution, and a saturated salt solution. The resulting organic phase was dried over magnesium sulfate and then concentrated under reduced pressure. The resulting residue was purified by silica gel column chromatography (elution solvent: hexane/ethyl acetate=90:10) to obtain 2-trimethylsilylethyl 3-O-ethoxymethyl-4,6-isopylidene-β-D-glucopyranoside as shown below (1.05 g, 2.78 mmol, 59%).

[Formula 31]

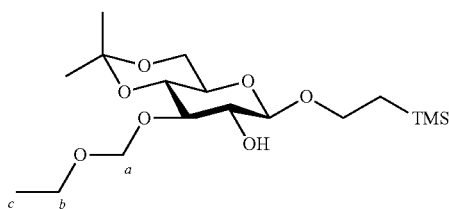

Furthermore, the analysis results of the obtained compound were as follows.

$[\alpha]_D^{23}$ −3.52 (c 0.885, CHCl$_3$); $^1$H NMR (400 MHz, CDCl$_3$): δ 4.88 (d, 1H, H-a, $J_{gem}$=6.8 Hz), 4.79 (d, 1H, H-a, $J_{gem}$=6.8 Hz), 4.39 (d, 1H, H-1, $J_{1,2}$=7.7 Hz), 3.97 (dt, 1H, OCH$_2$, $J_{OCH2,CH2Si}$=5.3 Hz, $J_{gem}$=9.7 Hz), 3.93 (dd, 1H, H-6a, $J_{5,6a}$=5.3 Hz, $J_{6a,6b}$=10.6 Hz), 3.79 (dd, 1H, H-6b, $J_{5,6b}$=10.2 Hz, $J_{6a,6b}$=10.6 Hz), 3.78 (t, 1H, H-3, $J_{2,3}$=$J_{3,4}$=8.7 Hz), 3.69 (d, 1H, OH, $J_{2,OH}$=1.9 Hz), 3.59-3.67 (m, 3H, OCH$_2$, H-b), 3.51 (t, 1H, H-4, $J_{3,4}$=$J_{4,5}$=8.7 Hz), 3.43 (ddd, 1H, H-2, $J_{1,2}$=7.7 Hz, $J_{2,3}$=8.7 Hz, $J_{2,OH}$=1.9 Hz), 3.25 (ddd, 1H, H-5, $J_{4,5}$=8.7 Hz, $J_{5,6a}$=5.3 Hz, $J_{5,6b}$=10.2 Hz), 1.49 (s, 3H, CH$_3$), 1.41 (s, 3H, CH$_3$), 1.24 (t, 3H, H-c, $J_{b,c}$=7.3 Hz), 0.94-1.12 (m, 2H, CH$_2$Si), 0.020 (s, 9H, SiCH$_3$); $^{13}$C NMR (100 MHz, CDCl$_3$): δ (102.9, 99.5 anomeric, isopropylidene), 96.3, 82.0, 74.0, 72.4, 67.6, 67.3, 63.9, 62.1, 29.1, 19.0, 18.3, 14.9, −1.49; FT-IR (neat): 3460, 1372, 1173, 1104, 1032, 860, 838 (cm$^{-1}$); HRMS (ESI-TOF) Calcd for C$_{21}$H$_{32}$O$_{11}$F$_8$S [M+NH$_4$]$^+$ 658.1570, found 658.1568.

Example 2-1-2

Synthesis of 2-trimethylsilylethyl 3-O-ethoxymethyl-4,6-isopylidene-β-D-mannopyranoside To a solution of 2-trimethylsilylethyl 3-O-ethoxymethyl-4,6-isopylidene-β-D-glucopyranoside (1.04 g, 2.75 mmol, 1.00 eq.) in dry methylene chloride (15.0 mL), were added sodium bicarbonate (461 mg, 5.49 mmol, 2.00 eq.) and a Dess-Martin oxidizing agent (1.75 g, 4.12 mmol, 1.50 eq.) at room temperature. The mixture was allowed to react at room temperature for 10 hours. Then, to the resulting reaction solution were added 10% aqueous sodium thiosulfate solution and saturated sodium bicarbonate with ice-cooling. The resulting aqueous phase was extracted with ethyl acetate, and then the organic phase was washed with 10% aqueous sodium thiosulfate solution, saturated sodium bicarbonate, and a saturated salt solution. The resulting organic phase was dried over magnesium sulfate and then concentrated under reduced pressure. The resulting residue was used for the next reaction.

To a solution of the residue in ethanol (28 mL), was added sodium borohydride (156 mg, 4.12 mmol, 1.50 eq.) with ice-cooling. The mixture was allowed to react for 15 minutes with ice-cooling and then poured into 1 M aqueous hydrochloric acid solution with ice-cooling. The aqueous phase was extracted with ethyl acetate solvent, and then the organic phase was washed with 1 M hydrochloric acid, a saturated aqueous sodium bicarbonate solution, and a saturated salt solution. The resulting organic phase was dried over magnesium sulfate and then concentrated under reduced pressure. The resulting residue was purified by silica gel column chromatography (elution solvent: hexane/ethyl acetate=75:25) to obtain 2-trimethylsilylethyl 3-O-ethoxymethyl-4,6-isopylidene-β-D-mannopyranoside as shown below (760 mg, 2.09 mmol, 76%).

[Formula 32]

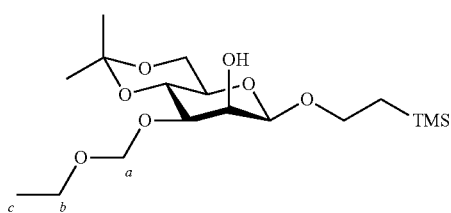

Furthermore, the analysis results of the obtained compound were as follows.

$[α]_D^{24}$ −22.8 (c 0.775, CHCl$_3$); $^1$H NMR (400 MHz, CDCl$_3$): δ 4.87 (d, 1H, H-a, $J_{gem}$=7.3 Hz), 4.81 (d, 1H, H-a, $J_{gem}$=7.3 Hz), 4.53 (br-s, 1H, H-1), 4.09 (br-d, 1H, H-2, $J_{2,3=3,4}$ Hz), 4.08 (dd, 1H, H-4, $J_{3,4}$=10.2 Hz, $J_{4,5}$=9.7 Hz), 4.01 (dt, 1H, OCH$_2$, $J_{OCH2,CH2Si}$=7.7 Hz, $J_{gem}$=9.2 Hz), 3.91 (dd, 1H, H-6a, $J_{5,6a}$=5.8 Hz, $J_{6a,6b}$=10.6 Hz), 3.86 (dd, 1H, H-6b, $J_{5,6b}$=10.2 Hz, $J_{6a,6b}$=10.6 Hz), 3.58-3.70 (m, 4H, H-3, OCH$_2$, H-b), 3.20 (ddd, 1H, H-5, $J_{4,5}$=9.7 Hz, $J_{5,6a}$=5.8 Hz, $J_{5,6b}$=10.2 Hz), 1.50 (s, 3H, CH$_3$), 1.40 (s, 3H, CH$_3$), 1.21 (t, 3H, H-c, $J_{b,c}$=7.3 Hz), 1.00 (t, 2H, CH$_2$Si, $J_{OCH2,CH2Si}$=7.7 Hz), 0.020 (s, 9H, SiCH$_3$); $^{13}$C NMR (100 MHz, CDCl$_3$): δ (99.6, 99.5 anomeric, isopropylidene), 94.5, 75.4, 70.5, 69.8, 67.8, 67.1, 63.2, 61.9, 29.0, 19.0, 18.0, 14.9, −1.62; FT-IR (neat): 3501, 1381, 1250, 1094, 1035, 862, 838 (cm$^{-1}$); HRMS (ESI-TOF) Calcd for C$_{21}$H$_{32}$O$_{11}$F$_8$S [M+NH$_4$]$^+$ 658.1570, found 658.1568.

Example 2-1-3

Synthesis of 2-trimethylsilylethyl 3-O-ethoxymethyl-4,6-isopylidene-2-O-(5-iodooctafluoro-3-oxapentanesulphonyl-β-D-mannopyranoside)

To a solution of 3-O-ethoxymethyl-4,6-isopylidene-β-D-mannopyranoside (750 mg, 1.98 mmol, 1.00 eq.) in dry THF, were added NaHMDS (2.60 mL, 2.58 mmol, 1.30 eq., 1.0 M in THF solution) with ice-cooling. The mixture was further stirred for 30 minutes, and then thereto was dropwise added 5-iodooctafluoro-3-oxapentanesulphonyl fluoride (1.00 g, 2.38 mmol, 1.20 eq.). The mixture was stirred for 30 minutes and then poured into 1 M hydrochloric acid with ice-cooling. The aqueous phase was extracted with ethyl acetate, and then the organic phase was washed with 1 M hydrochloric acid, a saturated aqueous sodium bicarbonate solution, and a saturated salt solution. The resulting organic phase was dried over magnesium sulfate and then concentrated under reduced pressure. The resulting residue was purified by silica gel column chromatography (elution solvent: hexane/ethyl acetate=90:10) to obtain 2-trimethylsilylethyl 3-O-ethoxymethyl-4,6-isopylidene-2-O-(5-iodooctafluoro-3-oxapentanesulfonyl-β-D-mannopyranoside as shown below (1.40 g, 1.78 mmol, 90%).

[Formula 33]

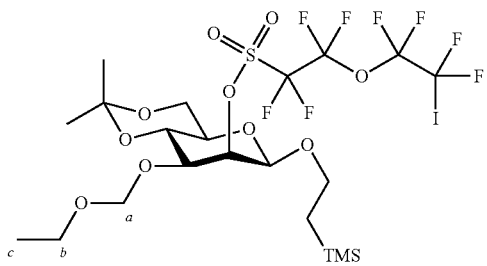

Furthermore, the analysis results of the obtained compound were as follows.

$[α]_D^{24}$ −31.2 (c 1.06, CHCl$_3$); $^1$H NMR (400 MHz, CDCl$_3$): δ 5.07 (br-d, 1H, H-2, $J_{2,3}$=2.9 Hz), 4.80 (d, 1H, H-a, $J_{gem}$=6.8 Hz), 4.72 (d, 1H, H-a, $J_{gem}$=6.8 Hz), 4.63 (br-s, 1H, H-1), 3.94 (dt, 1H, OCH$_2$, $J_{OCH2,CH2Si}$=7.7 Hz, $J_{gem}$=9.7 Hz), 3.94 (dd, 1H, H-6a, $J_{5,6a}$=5.8 Hz, $J_{6a,6b}$=9.7 Hz), 3.93 (dd, 1H, H-3, $J_{2,3}$=2.9 Hz, $J_{3,4}$=9.7 Hz), 3.92 (t, 1H, H-6b, $J_{5,6b}$=$J_{6a,6b}$=9.7 Hz), 3.86 (dd, 1H, H-4, $J_{3,4}$=9.7 Hz, $J_{4,5}$=10.2 Hz), 3.56-3.73 (m, 3H, OCH$_2$, H-b), 3.24 (ddd, 1H, H-5, $J_{4,5}$=10.2 Hz, $J_{5,6a}$=5.8 Hz, $J_{5,6b}$=9.7 Hz), 1.50 (s, 3H, CH$_3$), 1.39 (s, 3H, CH$_3$), 1.24 (t, 3H, H-c, $J_{b,c}$=6.8 Hz), 0.94-1.12 (m, 2H, CH$_2$Si), 0.014 (s, 9H, SiCH$_3$); $^{13}$C NMR (100 MHz, CDCl$_3$): δ (99.9, 97.5 anomeric, isopropylidene), 93.8, 84.1, 71.5, 70.0, 68.5, 67.7, 63.6, 61.8, 29.0, 19.1, 17.9, 14.9, −1.55; $^{19}$F NMR (373 MHz, CDCl$_3$): δ 10.7, −6.43, −10.0, −38.0; FT-IR (neat): 1731, 1415, 1296, 1199, 1150, 1120, 917, 863, 765 (cm$^{-1}$); HRMS (ESI-TOF) Calcd for C$_{21}$H$_{37}$NO$_{10}$SiSF$_8$ [M+NH$_4$]$^+$ 802.0820, found 802.0825.

Example 2-1-4

Synthesis of 2-trimethylsilylethyl 3-O-ethoxymethyl-4,6-isopylidene-2-O-(9-carboxyl 3-oxa-1,1,2,2,4,4,5,5-octafluoro-7-iodo-6-nonenesulfonyl-β-D-mannopyranoside)

To a solution of 2-trimethylsilylethyl 3-O-ethoxymethyl-4,6-isopylidene-2-O-(5-iodooctafluoro-3-oxapentanesulfonyl-β-D-mannopyranoside (545 mg, 695 µmol, 1.00 eq.) and 4-pentynoic acid (102 mg, 1.04 mmol, 1.50 eq.) in CH$_3$CN (6.00 mL) and H$_2$O (6.00 mL), were added sodium bicarbonate (87.4 mg, 1.04 mmol, 1.50 eq.) and sodium thiosulfate Na$_2$S$_2$O$_4$ (181 mg, 1.04 mmol, 1.50 eq.), and the resulting mixture was allowed to react at room temperature for 1.5 hours. The resulting reaction solution was poured into water, and the organic phase was extracted with ethyl acetate. The resulting organic phase was washed with saturated sodium bicarbonate and a saturated salt solution. The washed organic phase was dried over magnesium sulfate and then concentrated under reduced pressure. The resulting residue was purified by silica gel column chromatography (elution solvent: chloroform/methanol=99:1) to obtain 2-trimethylsilylethyl 3-O-ethoxymethyl-4,6-isopylidene-2-O-(9-carboxyl 3-oxa-1,1,2,2,4,4,5,5-octafluoro-7-iodo-6-nonenesulfonyl-β-D-mannopyranoside as shown below (530 mg, 601 µmol, 86%).

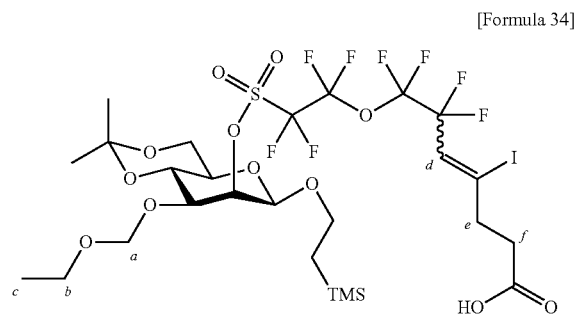

[Formula 34]

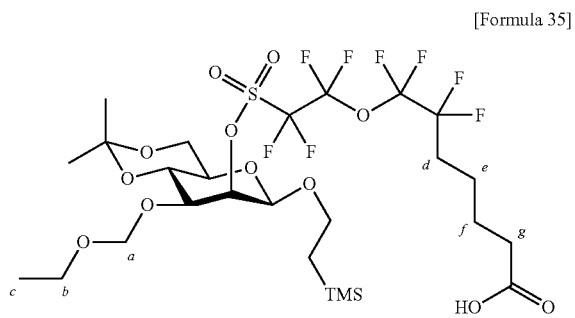

[Formula 35]

Furthermore, the analysis results of the obtained compound were as follows.

$^1$H NMR (400 MHz, CDCl$_3$): δ 6.38 (t, 1H, H-d, J$_{d,F}$=14.2 Hz), 5.07 (br-d, 1H, H-2, J$_{2,3}$=2.9 Hz), 4.81 (d, 1H, H-a, J$_{gem}$=7.3 Hz), 4.74 (d, 1H, H-a, J$_{gem}$=7.3 Hz), 4.64 (br-s, 1H, H-1), 3.96 (dt, 1H, OCH$_2$, J$_{OCH2,CH2Si}$=7.7 Hz, J$_{gem}$=9.7 Hz), 3.95 (dd, 1H, H-3, J$_{2,3}$=2.9 Hz, J$_{3,4}$=9.7 Hz), 3.95 (dd, 1H, H-6a, J$_{5,6a}$=5.8 Hz, J$_{6a,6b}$=9.7 Hz), 3.92 (t, 1H, H-6b, J$_{5,6b}$=J$_{6a,6b}$=9.7 Hz), 3.87 (dd, 1H, H-4, J$_{3,4}$=9.7 Hz, J$_{4,5}$=9.2 Hz), 3.57-3.76 (m, 3H, OCH$_2$, H-b), 3.25 (ddd, 1H, H-5, J$_{4,5}$=9.2 Hz, J$_{5,6a}$=5.8 Hz, J$_{5,6b}$=9.7 Hz), 3.00 (t, 2H, H-e, J$_{e,f}$=7.7 Hz), 2.63 (t, 2H, H-f, J$_{e,f}$=7.7 Hz), 1.50 (s, 3H, CH$_3$), 1.39 (s, 3H, CH$_3$), 1.21 (t, 3H, H-c, J$_{b,c}$=7.3 Hz), 1.00 (dt, 2H, CH$_2$Si, J$_{OCH2,CH2Si}$=7.7 Hz, J$_{gem}$=9.7 Hz), 0.022 (s, 9H, SiCH$_3$); $^{19}$F NMR (373 MHz, CDCl$_3$): δ −6.43, −12.4, −34.3 (d, J$_{d,F}$=14.2 Hz), −38.1; FT-IR (neat): 3411, 1719, 1641, 1411, 1305, 1117, 1080, 924, 838 (cm$^{-1}$); HRMS (ESI-TOF) Calcd for C$_{21}$H$_{37}$NO$_{10}$SiSF$_8$ [M+NH$_4$]$^+$ 802.0820, found 802.0825.

Example 2-1-5

Synthesis of 2-trimethylsilylethyl 3-O-ethoxymethyl-4,6-isopylidene-2-O-(9-carboxyl 3-oxa-1,1,2,2,4,4,5,5-octafluoro-nonanesulfonyl-β-D-mannopyranoside)

To a solution of 2-trimethylsilylethyl 3-O-ethoxymethyl-4,6-isopylidene-2-O-(9-carboxyl 3-oxa-1,1,2,2,4,4,5,5-octafluoro-7-iodo-6-nonenesulfonyl-β-D-mannopyranoside (920 mg, 1.04 mmol, 1.00 eq.) in a mixture of MeOH (10.0 mL) and H$_2$O (4.00 mL), were added sodium bicarbonate (262 mg, 3.13 mmol, 3.00 eq.) and Pd/C (500 mg). The mixture was allowed to react in a hydrogen atmosphere for 18 hours. The palladium catalyst was removed by filtration, and then the reaction solution was poured into water. The aqueous phase was extracted with ethyl acetate, and then the organic phase was washed with saturated sodium bicarbonate and a saturated salt solution. The resulting organic phase was dried over magnesium sulfate and concentrated under reduced pressure. The resulting residue was purified by silica gel column chromatography (elution solvent: chloroform/methanol=99:1) to obtain 2-trimethylsilylethyl 3-O-ethoxymethyl-4,6-isopylidene-2-O-(9-carboxyl 3-oxa-1,1,2,2,4,4,5,5-octafluoro-nonanesulfonyl-β-D-mannopyranoside as shown below (767 mg, 990 μmol, 95%).

Furthermore, the analysis results of the obtained compound were as follows.

[α]$_D^{25}$ −32.3 (c 0.715, CHCl$_3$); $^1$H NMR (400 MHz, CDCl$_3$): δ 5.07 (br-d, 1H, H-2, J$_{2,3}$=2.9 Hz), 4.81 (d, 1H, H-a, J$_{gem}$=6.8 Hz), 4.75 (d, 1H, H-a, J$_{gem}$=6.8 Hz), 4.63 (br-s, 1H, H-1), 3.96 (dt, 1H, OCH$_2$, J$_{OCH2,CH2Si}$=9.4 Hz, J$_{gem}$=9.7 Hz), 3.93 (dd, 1H, H-3, J$_{2,3}$=2.9 Hz, J$_{3,4}$=9.2 Hz), 3.93 (dd, 1H, H-6a, J$_{5,6a}$=5.8 Hz, J$_{6a,6b}$=10.2 Hz), 3.92 (t, 1H, H-6b, J$_{5,6b}$=J$_{6a,6b}$=10.2 Hz), 3.87 (dd, 1H, H-4, J$_{3,4}$=9.2 Hz, J$_{4,5}$=9.7 Hz), 3.57-3.75 (m, 3H, OCH$_2$, H-b), 3.25 (ddd, 1H, H-5, J$_{4,5}$=9.7 Hz, J$_{5,6a}$=5.8 Hz, J$_{5,6b}$=10.2 Hz), 2.40 (t, 2H, H-g, J$_{f,g}$=7.3 Hz), 2.09 (tt, 2H, H-d, J$_{d,e}$=7.3 Hz, J$_{d,F}$=18.3 Hz), 1.60-1.76 (m, 4H, H-e, H-f), 1.50 (s, 3H, CH$_3$), 1.39 (s, 3H, CH$_3$), 1.21 (t, 3H, H-c, J$_{b,c}$=7.3 Hz), 0.99 (t, 2H, CH$_2$S$_1$, J$_{OCH2,CH2Si}$=9.4 Hz), 0.015 (s, 9H, SiCH$_3$); $^{13}$C NMR (100 MHz, CDCl$_3$): δ 178.5, (100.0, 97.5 anomeric, isopylidene), 93.6, 84.0, 83.9, 71.5, 70.0, 68.4, 67.7, 63.6, 61.8, 33.4, 32.0, 30.1 (t, C-d, J$_{C-d,F}$=22.1 Hz), 28.9, 26.7, 24.0, 19.9, 19.0, 17.8, 14.8, −1.63; $^{19}$F NMR (373 MHz, CDCl$_3$): δ −6.73, −12.8, −38.3, −42.8; FT-IR (neat): 1713, 1413, 1179, 1116, 1021, 920, 863 (cm$^{-1}$); HRMS (ESI-TOF) Calcd for C$_{21}$H$_{37}$NO$_{10}$ SiSF$_8$ [M+NH$_4$]$^+$ 802.0820, found 802.0825.

Example 2-1-6

Synthesis of 2-FDG Monomer

To a solution of 2-trimethylsilylethyl 3-O-ethoxymethyl-4,6-isopylidene-2-O-(9-carboxyl 3-oxa-1,1,2,2,4,4,5,5-octafluoro-nonanesulfonyl-β-D-mannopyranoside (657 mg, 0.866 mmol, and 1.00 eq.) and 1-amino-5,6-heptadiene (144 mg, 1.30 mmol, 1.50 eq.) in dry methylene chloride, were added HATU (395 mg, 1.04 mmol, 1.20 eq.), diisopropylethylamine DIEA (270 μL, 1.56 mmol, 1.80 eq.), and a catalytic amount of DMAP at room temperature. The mixture was allowed to react at room temperature for 20 minutes, and then insoluble matter was filtered. The filtrate was concentrated under reduced pressure. The resulting residue was purified by silica gel column chromatography (elution solvent: chloroform/methanol=99:1) to obtain the 2-FDG monomer as shown below (634 mg, 0.745 mmol, 86%).

39

[Formula 36]

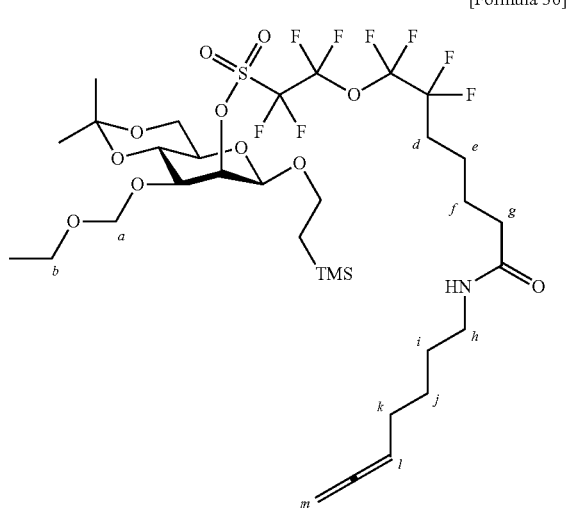

Furthermore, the analysis results of the obtained compound were as follows.

$[\alpha]_D^{24}$ −31.0 (c 1.00, CHCl$_3$); $^1$H NMR (400 MHz, CDCl$_3$): δ 5.48 (br-s, 1H, NH), 5.08 (tt, 1H, H-1, $J_{k,l}$=$J_{l,m}$=6.8 Hz), 5.06 (br-d, 1H, H-2, $J_{2,3}$=2.4 Hz), 4.80 (d, 1H, H-a, $J_{gem}$=6.8 Hz), 4.72 (d, 1H, H-a, $J_{gem}$=6.8 Hz), 4.66 (dt, 2H, H-m, $J_{l,m}$=6.8 Hz, $J_{k,m}$=3.9 Hz), 4.63 (br-s, 1H, H-1), 3.95 (ddd, 1H, OCH$_2$, $J_{OCH2,CH2Si}$=8.2 Hz, $J_{gem}$=8.7 Hz), 3.94 (dd, 1H, H-3, $J_{2,3}$=2.4 Hz, $J_{3,4}$=9.7 Hz), 3.93 (dd, 1H, H-6a, $J_{5,6a}$=5.8 Hz, $J_{6a,6b}$=10.2 Hz), 3.90 (t, 1H, H-6b, $J_{5,6b}$=9.2 Hz, $J_{6a,6b}$=10.2 Hz), 3.85 (dd, 1H, H-4, $J_{3,4}$=9.7 Hz, $J_{4,5}$=10.2 Hz), 3.56-3.75 (m, 3H, OCH$_2$, H-b), 3.26 (t, 2H, H-h, $J_{h,i}$=7.3 Hz), 3.25 (ddd, 1H, H-5, $J_{4,5}$=10.2 Hz, $J_{5,6a}$=5.8 Hz, $J_{5,6b}$=9.2 Hz), 2.18 (tt, 2H, H-g, $J_{f,g}$=7.7 Hz), 2.07 (tt, 2H, H-d, $J_{d,e}$=6.8 Hz, $J_{d,F}$=17.9 Hz), 2.02 (dtt, 2H, H-k, $J_{j,k}$=$J_{k,l}$=6.8 Hz, $J_{k,m}$=3.9 Hz), 1.73 (tt, 2H, H-i, $J_{h,i}$=7.3 Hz, $J_{i,j}$=6.8 Hz), 1.42-1.64 (m, 9H, H-e, H-f, H-j, CH$_3$), 1.39 (s, 3H, CH$_3$), 1.20 (t, 3H, H-c, $J_{b,c}$=7.3 Hz), 0.99 (t, 2H, CH$_2$Si, $J_{OCH2,CH2Si}$=8.2 Hz), 0.015 (s, 9H, SiCH$_3$); $^{13}$C NMR (100 MHz, CDCl$_3$): δ 208.5, 172.0, (99.9, 97.5 anomeric, isopropylidene), 93.8, 89.4, 84.1, 74.8, 71.5, 70.0, 68.4, 67.7, 63.5, 61.8, 39.3, 35.9, 30.0 (t, C-d, $J_{C-d,F}$=22.1 Hz), 29.0, 27.7, 26.2, 24.9, 19.8, 19.0, 17.8, 14.8, −1.62; $^{19}$F NMR (373 MHz, CDCl$_3$): δ −6.68, −12.9, −38.2, −43.0 (t, $J_{d,F}$=17.9 Hz); FT-IR (neat): 1950, 1652, 1411, 1218, 1096, 1021, 920, 779 (cm$^{-1}$); HRMS (ESI-TOF) Calcd for C$_{33}$H$_{54}$NO$_{11}$SiSF$_5$ [M+H]$^+$ 852.3044, found 852.3059.

40

Example 2-2

Synthesis of 2-FDG Copolymer

The synthesis steps of 2-FDG copolymer are shown below.

[Formula 37]

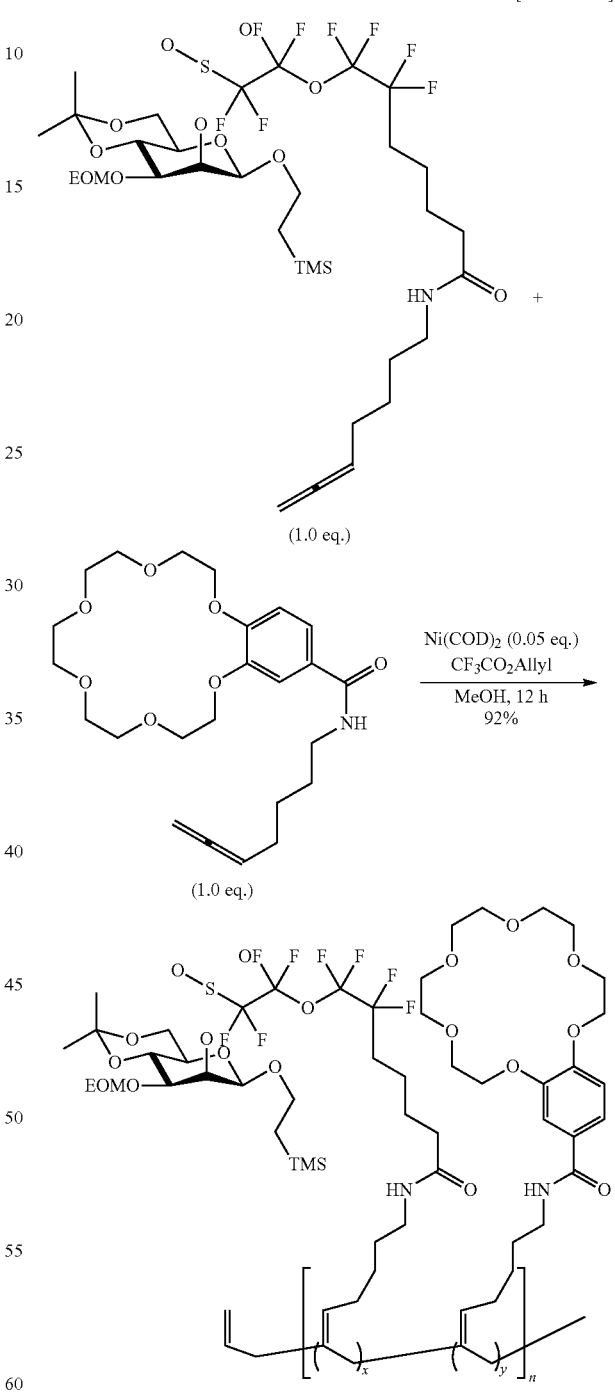

To a mixed solution of a toluene solution of 0.10 M bis(1,5-cyclooctadiene)nickel (120 µL, 12.0 µmol, 0.0500 eq.) and a toluene solution of 1.0 M allyl trifluoroacetate (19.3 µL, 19.3 µmol, 0.0800 eq.), was added a solution of 2-FDG monomer (205 mg, 241 µmol, 1.00 eq.) and a crown ether allene monomer (103 mg, 133 µmol, 1.00 eq.) in MeOH (0.700 mL)

in a nitrogen atmosphere. After verifying reaction completion by TLC, the reaction solution was diluted with hexane to precipitate a purified product. The resulting precipitate was filtered to obtain the 2-FDG copolymer as shown below. (283 mg, 222 μmol, 92%, 2-FDG:Crown Ether=1:1.04)

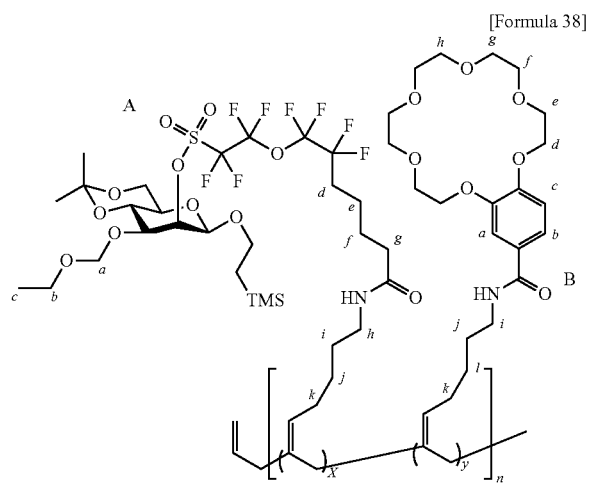

[Formula 38]

Furthermore, the analysis results of the obtained compound were as follows.

$^1$H NMR (400 MHz, CDCl$_3$): δ 7.47 (br-s, 2H, B-b, B-c), 6.75 (br-s, 1H, B-a), 5.19 (br-s, 2H, =C—CH—), 5.05 (br-s, 1H, A-2), 4.77 (br-d, 1H, A-a, J$_{gem}$=7.3 Hz), 4.71 (br-d, 1H, A-a, J$_{gem}$=7.3 Hz), 4.63 (br-s, 1H, A-1), 4.09 (br-s, 4H, B-d, B-d'), 3.55-3.96 (m, 24H, A-3, A-4, A-6a, A-6b, A-b, OCH$_2$, B-e, B-e', B-f, B-f', B-g, B-g', B-h, B-h'), 3.35 (br-s, 2H, B-i), 3.16-3.26 (m, 3H, A-5, A-h), 2.55 (br-s, 4H, =C—CH$_2$—C=), 2.21 (br-s, 2H, A-g), 1.98 (br-s, 6H, A-d, A-k, B-1), 1.25-1.63 (m, 15H, A-e, A-f, A-i, A-j, B-j, B-k, CH$_3$), 1.17 (br-t, 3H, A-c, J$_{b,c}$=6.8 Hz), 0.99 (br-t, 2H, CH$_2$Si, J$_{OCH2, CH2Si}$=8.7 Hz), -0.0093 (s, 9H, SiCH$_3$); $^{19}$F NMR (373 MHz, CDCl$_3$): δ -7.53, -13.4, -39.5, -43.4; FT-IR (neat): 3319, 2929, 1644, 1507, 1265, 1121, 758 (cm$^{-1}$).

Example 2-3

Removal of 2-FDG

The removal steps of 2-FDG are shown below.

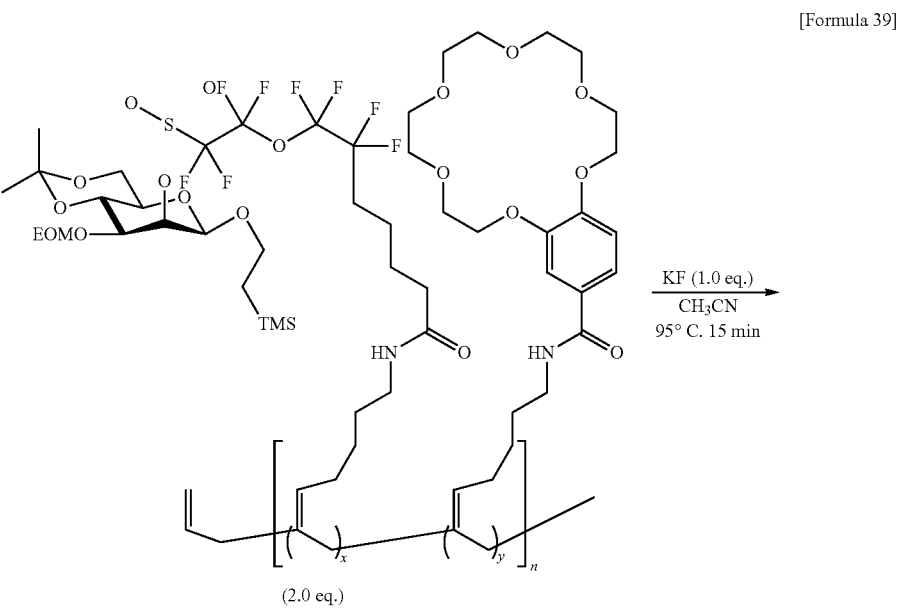

[Formula 39]

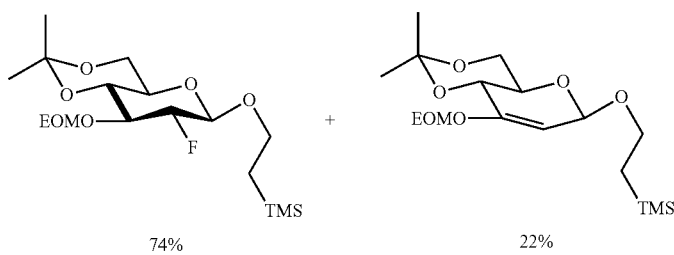

To a solution of the synthesized copolymer (43.6 mg, 33.5 µmol, 2.00 eq.) in acetonitrile CH₃CN (370 µL), was added an aqueous solution of KF (10.0 µL, 16.7 µmol, and 1.00 eq., 1.67 M in H₂O solution), and the mixture was heated at 95 degrees for 15 minutes. The resulting residue was purified by silica gel column chromatography (elution solvent: hexane/ethyl acetate=80:20) to obtain 2-trimethylsilylethyl 2-deoxy-3-O-ethoxymethyl-2-fluoro-4,6-O-isopropylidene-β-D-glucopyranoside (4.80 mg, 12.4 µmol, 74% based on KF) and 2-trimethylsilylethyl 2-deoxy-3-O-ethoxymethyl-4,6-O-isopropylidene-β-D-erythro-hex-2-enepyranoside as shown below (1.40 mg, 3.90 µmol, 22% based on KF).

[Formula 40]

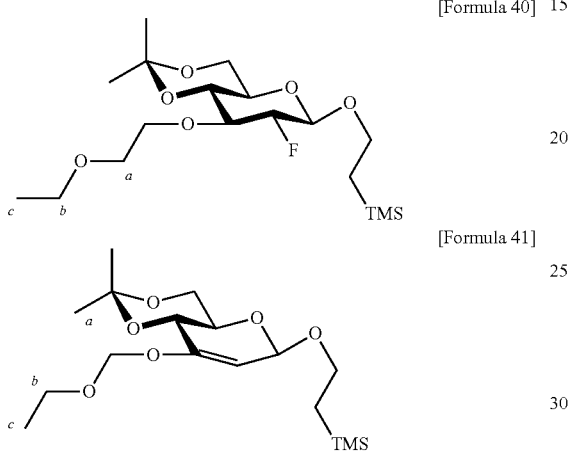

[Formula 41]

The analysis results of 2-trimethylsilylethyl 2-deoxy-3-O-ethoxymethyl-2-fluoro-4,6-O-isopropylidene-β-D-glucopyranoside were as follows.

$[\alpha]_D^{17}$ +50.1 (c 0.940, CHCl₃); ¹H NMR (400 MHz, CDCl₃): δ 4.86 (d, 1H, H-a, $J_{gem}$=6.8 Hz), 4.79 (d, 1H, H-a, $J_{gem}$=6.8 Hz), 4.53 (dd, 1H, H-1, $J_{1,2}$=7.7 Hz, $J_{1,F}$=4.4 Hz), 4.19 (ddd, 1H, H-2, $J_{1,2}$=7.7 Hz, $J_{2,3}$=8.7 Hz, $J_{2,F}$=49.8 Hz), 4.00 (dd, 1H, H-6a, $J_{5,6a}$=5.3 Hz, $J_{6a,6b}$=10.6 Hz), 3.96 (dt, 1H, OCH₂, $J_{OCH2,CH2Si}$=5.8 Hz, $J_{gem}$=9.7 Hz), 3.88 (ddd, 1H, H-3, $J_{2,3}$=8.7 Hz, $J_{3,4}$=9.2 Hz, $J_{3,F}$=15.0 Hz), 3.76 (dd, 1H, H-6b, $J_{5,6b}$=10.2 Hz, $J_{6a,6b}$=10.6 Hz), 3.63-3.69 (m, 3H, OCH₂, H-b), 3.59 (dd, 1H, H-4, $J_{3,4}$=9.2 Hz, $J_{4,5}$=9.7 Hz), 3.26 (ddd, 1H, H-5, $J_{4,5}$=9.7 Hz, $J_{5,6a}$=5.3 Hz, $J_{5,6b}$=10.2 Hz), 1.48 (s, 3H, CH₃), 1.40 (s, 3H, CH₃), 1.21 (t, 3H, H-c, $J_{b,c}$=6.8 Hz), 0.93-1.09 (m, 2H, CH₂Si), 0.022 (s, 9H, SiCH₃); ¹³C NMR (100 MHz, CDCl₃): δ 100.8 (d, anomeric, $J_{C-1,F}$=24.4 Hz), 99.4 (isopropylidene), 95.1, 92.5 (d, C-2, $J_{C-2,F}$=187 Hz), 75.6 (d, C-3, $J_{C-3,F}$=19.0 Hz), 72.7 (d, C-4, $J_{C-4,F}$=9.2 Hz), 67.9, 67.2, 63.2, 62.0, 29.0, 19.0, 18.1, 14.8, −1.45; ¹⁹F NMR (373 MHz, CDCl₃): δ −123.1 (dd, $J_{2,F}$=49.8 Hz, $J_{3,F}$=15.0 Hz); FT-IR (neat): 1380, 1250, 1174, 1096, 858, 756 (cm⁻¹); HRMS (ESI-TOF) Calcd for C₁₇H₃₇NO₆SiF [M+NH₄]⁺ 398.2376, found 398.2374.

The analysis results of 2-trimethylsilylethyl 2-deoxy 3-O-ethoxymethyl-4,6-O-isopropylidene-β-D-erythro-hex-2-enepyranoside were as follows.

$[\alpha]_D^{17}$ +50.1 (c 0.940, CHCl₃); ¹H NMR (400 MHz, CDCl₃): δ 5.38 (br-d, 1H, H-2 $J_{2,4}$=1.9 Hz), 5.09 (br-s, 2H, H-a), 4.95 (br-s, 1H, H-1), 4.46 (br-dt, 1H, H-4, $J_{2,4}$=$J_{4,6a}$=1.9 Hz, $J_{4,5}$=9.2 Hz), 3.92 (dd, 1H, H-6a, $J_{5,6a}$=6.3 Hz, $J_{6a,6b}$=10.6 Hz), 3.88 (dt, 1H, OCH₂, $J_{OCH2,CH2Si}$=6.3 Hz, $J_{gem}$=9.7 Hz), 3.86 (t, 1H, H-6b, $J_{5,6b}$=$J_{6a,6b}$=10.6 Hz), 3.67 (q, 2H, H-b, $J_{b,c}$=7.3 Hz), 3.60 (ddd, 1H, H-5, $J_{4,5}$=9.2 Hz, $J_{5,6a}$=6.3 Hz, $J_{5,6b}$=10.6 Hz), 3.56 (dt, 1H, OCH₂, $J_{OCH2,CH2Si}$=6.3 Hz, $J_{gem}$=9.7 Hz), 1.54 (s, 3H, CH₃), 1.47 (s, 3H, CH₃), 1.21 (t, 3H, H-c, $J_{b,c}$=7.3 Hz), 0.95-1.00 (m, 2H, CH₂Si), 0.016 (s, 9H, SiCH₃); FT-IR (neat): 1660, 1374, 1217, 1086, 859, 767 (cm⁻¹); HRMS (ESI-TOF) Calcd for C₂₄H₃₉N₂O₇ [M+Na]⁺ 467.2758, found 467.2757.

Example 2-4

Deprotection

The deprotection steps of 2-FDG are shown below.

[Formula 42]

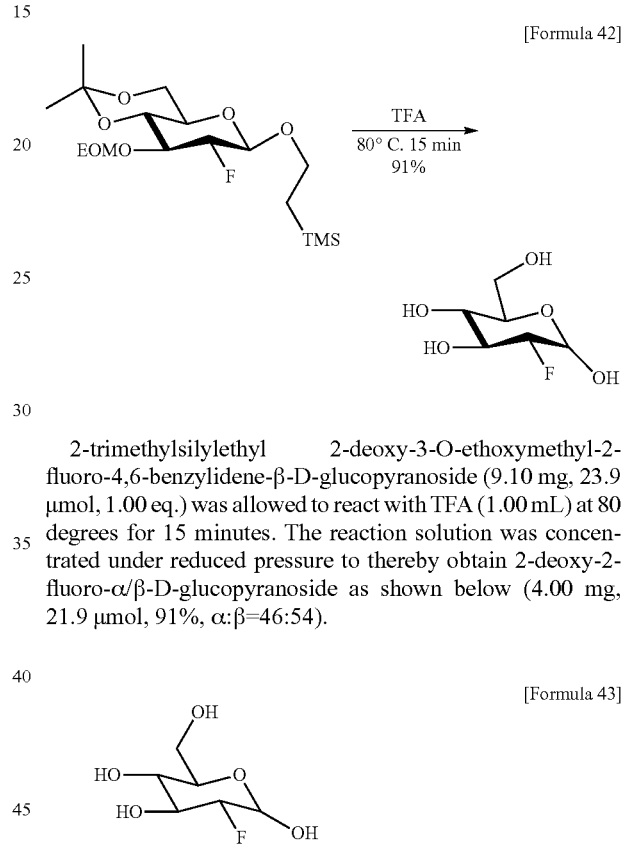

2-trimethylsilylethyl 2-deoxy-3-O-ethoxymethyl-2-fluoro-4,6-benzylidene-β-D-glucopyranoside (9.10 mg, 23.9 µmol, 1.00 eq.) was allowed to react with TFA (1.00 mL) at 80 degrees for 15 minutes. The reaction solution was concentrated under reduced pressure to thereby obtain 2-deoxy-2-fluoro-α/β-D-glucopyranoside as shown below (4.00 mg, 21.9 µmol, 91%, α:β=46:54).

[Formula 43]

Furthermore, the analysis results of the obtained compound were as follows.

¹H NMR (400 MHz, D₂O): δ 5.41 (br-d, 1H, H-1α, $J_{1,2}$=3.9 Hz), 4.87 (dd, 1H, H-1β, $J_{1,2}$=7.7 Hz, $J_{1,F}$=2.4 Hz), 4.39 (ddd, 1H, H-2α, $J_{1,2}$=3.9 Hz, $J_{2,3}$=9.7 Hz, $J_{2,F}$=51.5 Hz), 4.07 (ddd, 1H, H-2β, $J_{1,2}$=7.7 Hz, $J_{2,3}$=9.2 Hz, $J_{2,F}$=52.5 Hz), 3.93 (ddd, 1H, H-3α, $J_{2,3}$=9.7 Hz, $J_{3,4}$=9.2 Hz, $J_{3,F}$=15.5 Hz), 3.90 (br-d, 1H, H-6aβ, $J_{6a,6b}$=12.1 Hz), 3.83 (dt, 1H, H-5α, $J_{4,5}$=9.7 Hz, $J_{5,6a}$=$J_{5,6b}$=5.3 Hz), 3.76 (ddd, 1H, H-3β, $J_{2,3}$=9.2 Hz, $J_{3,4}$=9.7 Hz, $J_{3,F}$=15.0 Hz), 3.73 (dd, 1H, H-6aα, $J_{5,6a}$=5.3 Hz, $J_{6a,6b}$=12.6 Hz), 3.68 (dd, 1H, H-6bβ, $J_{5,6b}$=5.3 Hz, $J_{6a,6b}$ 12.1 Hz), 3.67 (dd, 1H, H-6bα, $J_{5,6b}$=5.3 Hz, $J_{6a,6b}$=12.6 Hz), 3.41-3.50 (m, 3H, H-4α, H-4β, H-5β); ¹⁹F NMR (373 MHz, CDCl₃): δ −202.9 (dd, Fα, $J_{2,F}$=51.5 Hz, $J_{3,F}$=15.5 Hz), −203.1 (dd, Fβ, $J_{2,F}$=52.5 Hz, $J_{3,F}$=15.0 Hz); FT-IR (neat): 3428, 1670, 1469, 1077, 771, 623, 478 (cm⁻¹); HRMS (ESI-TOF) Calcd for C₂₄H₃₉N₂O₇ [M+Na]⁺ 467.2758, found 467.2757.

Example 3

Deprotection of 3-FDG

The deprotection steps of 3-FDG are shown below.

[Formula 44]

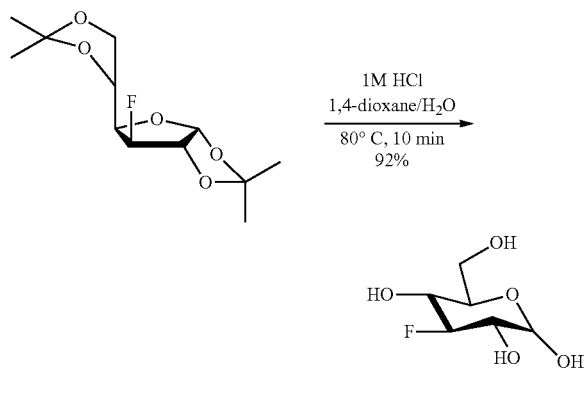

To a solution of 3-deoxy-3-fluoro-1,2,5,6-di-O-isopropylidene-α-D-glucofuranose (36.0 mg, 137 μmol, 1.00 eq.) in a mixture of 1,4-dioxane (680 μL) and H₂O (680 μL), was added 4 M aqueous hydrochloric acid solution (680 μL). The mixture was allowed to react at 80 degrees for 10 minutes and then concentrated under reduced pressure to obtain 3-deoxy-3-fluoro-α/β-D-glucopyranose as shown below (22.9 mg, 126 μmol, 92%, α:β=45:55).

[Formula 45]

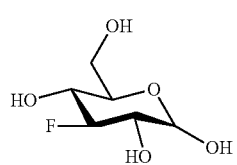

Furthermore, the analysis results of the obtained compound were as follows.

¹H NMR (400 MHz, D₂O): δ 5.24 (t, 1H, H-1α, $J_{1,2}=J_{1,F}=3.9$ Hz), 4.65 (d, 1H, H-1β, $J_{1,2}=8.2$ Hz), 4.58 (dt, 1H, H-3α, $J_{2,3}=J_{3,4}=9.2$ Hz $J_{3,F}=54.6$ Hz), 4.35 (ddd, 1H, H-3β, $J_{2,3}=9.2$ Hz, $J_{3,4}=8.7$ Hz, $J_{3,F}=53.2$ Hz), 3.87 (br-d, 1H, H-6aβ, $J_{6a,6b}=12.6$ Hz), 3.85 (dd, 1H, H-6aα, $J_{5,6a}=5.3$ Hz, $J_{6a,6b}=10.6$ Hz), 3.79 (ddd, 1H, H-2α, $J_{1,2}=3.9$ Hz, $J_{2,3}=9.2$ Hz, $J_{2,F}=15.5$ Hz), 3.79 (dd, 1H, H-6bα, $J_{5,6b}=5.3$ Hz, $J_{6a,6b}=10.6$ Hz), 3.79 (dt, 1H, H-5α, $J_{4,5}=9.7$ Hz, $J_{5,6a}=J_{5,6b}=5.3$ Hz), 3.76 (dd, 1H, H-6bβ, $J_{5,6b}=5.3$ Hz, $J_{6a,6b}=12.6$ Hz), 3.70 (ddd, 1H, H-4α, $J_{3,4}=9.2$ Hz, $J_{4,5}=9.7$ Hz, $J_{4,F}=14.2$ Hz), 3.69 (ddd, 1H, H-4β, $J_{3,4}=8.7$ Hz, $J_{4,5}=9.7$ Hz $J_{4,F}=14.2$ Hz), 3.50 (ddd, 1H, H-2β, $J_{1,2}=8.2$ Hz, $J_{2,3}=9.2$ Hz $J_{2,F}=14.2$ Hz), 3.45 (dt, 1H, H-5β, $J_{4,5}=9.7$ Hz, $J_{5,6a}=J_{5,6b}=5.3$ Hz); ¹⁹F NMR (373 MHz, D₂O): δ -119.7 (ddd, Fα, $J_{2,F}=13.5$ Hz, $J_{3,F}=54.6$ Hz, $J_{4,5}=14.2$ Hz), -124.6 (ddd, Fβ, $J_{3,F}=53.2$ Hz, $J_{2,F}=J_{4,F}=14.2$ Hz); FT-IR (neat): 3261, 1585, 1382, 1041, 684, 516 (cm⁻¹); HRMS (ESI-TOF) Calcd for $C_{24}H_{39}N_2O_7$ [M+Na]⁺ 467.2758, found 467.2757.

Example 4

Production of 3-FDG Using Solid Phase-Supported Copolymer

Example 4-1

Synthesis of Linker

The synthesis steps of a linker are shown below.

[Formula 46]

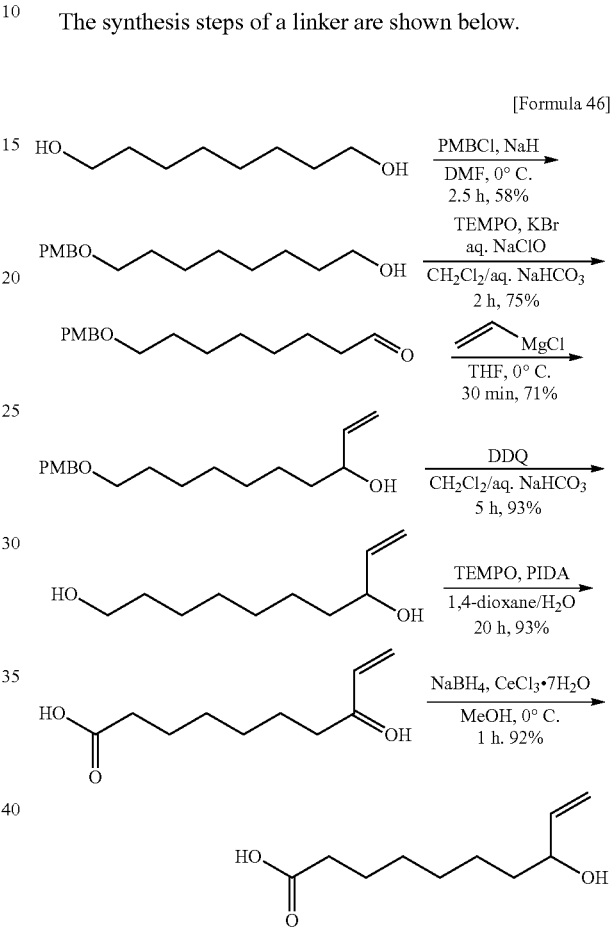

Example 4-1-1

Synthesis of 8-((4-methoxybenzyl)oxy)octan-1-ol

The oil attached to 63 wt % sodium hydride (1.14 g, 30.1 mmol, 1.00 eq.) was washed three times with hexane and removed. Subsequently, thereto were added dry DMF (30.0 mL) and 1,8-octanediol (4.40 g, 30.1 mmol, 1.00 eq.) at 0 degrees. The mixture was allowed to react for 5 minutes with ice-cooling, and then thereto was dropwise added a solution of PMBCl (4.08 mL, 30.1 mmol, 1.00 eq.) in dry DMF (20.0 mL) over 1 hour. The reaction mixture was allowed to react for further 1.5 hours and then poured into an aqueous ammonium chloride solution with ice-cooling, and the organic phase was extracted with ethyl acetate. The resulting organic phase was washed with 1 M hydrochloric acid, saturated sodium bicarbonate, and a saturated salt solution. The washed organic phase was dried over magnesium sulfate and then concentrated under reduced pressure. The resulting residue was purified by silica gel column chromatography (elution solvent: hexane/ethyl acetate=75:25) to obtain 8-((4-methoxybenzyl)oxy)octa-1-nol as shown below (4.66 g, 17.5 mmol, 58%).

[Formula 47]

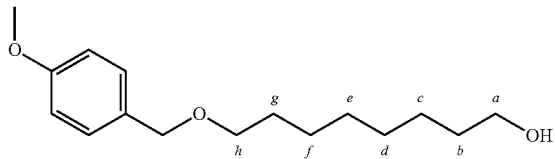

Furthermore, the analysis results of the obtained compound were as follows.

$^1$H NMR (400 MHz, CDCl$_3$): δ 7.26 (d, 2H, aromatic, J=9.2 Hz), 6.88 (d, 2H, aromatic, J=9.2 Hz), 4.43 (br-s, 2H, 4-MeOBn), 3.80 (s, 3H, Me), 3.63 (t, 2H, H-h, $J_{g,h}$=6.8 Hz), 3.43 (t, 2H, H-a, $J_{a,b}$=6.8 Hz), 1.52-1.63 (m, 4H, H-b, H-g), 1.27-1.39 (m, 8H, H-c, H-d, H-e, H-f); $^{13}$C NMR (100 MHz, CDCl$_3$): δ 129.2, 113.7, 72.5, 70.1, 63.0, 55.3, 32.7, 29.7, 29.4, 29.3, 26.1, 25.6; FT-IR (neat): 2874, 1598, 1355, 1177, 1098, 923, 664, 555 (cm$^{-1}$); HRMS (ESI-TOF) Calcd for C$_{24}$H$_{39}$N$_2$O$_7$ [M+Na]$^+$ 467.2758, found 467.2757.

Example 4-1-2

Synthesis of 8-((4-methoxybenzyl)oxy)octa-1-nol

To a solution of 8-((4-methoxybenzyl)oxy)octa-1-nol (4.00 g, 15.0 mmol, 1.00 eq.) in a mixture of methylene chloride CH$_2$Cl$_2$ (22.5 mL) and saturated sodium bicarbonate (15.0 mL), were added catalytic amount of TEMPO, KBr, and sodium hypochlorite (30.0 mL) at room temperature. The mixture was allowed to react at room temperature for 2 hours, and then thereto were added 10% aqueous sodium thiosulfate solution and a saturated salt solution. The organic phase was extracted with ethyl acetate, and then the resulting organic phase was washed with 10% aqueous sodium thiosulfate solution, saturated sodium bicarbonate, and a saturated salt solution. The washed organic phase was dried over magnesium sulfate and then concentrated under reduced pressure. The resulting residue was purified by silica gel column chromatography (elution solvent: hexane/ethyl acetate=97:3) to obtain 8-((4-methoxybenzyl)oxy)octa-1-nal as shown below (2.98 g, 11.3 mmol, 75%).

[Formula 48]

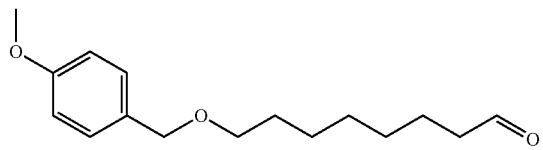

Furthermore, the analysis results of the obtained compound were as follows.

$^1$H NMR (400 MHz, CDCl$_3$): δ 7.79 (d, 4H, H-c, $J_{b,c}$=8.2 Hz), 7.34 (d, 4H, H-b, $J_{b,c}$=8.2 Hz), 4.15 (t, 4H, H-d, $J_{d,e}$=4.8 Hz), 3.68 (t, 4H, H-e, $J_{d,e}$=4.8 Hz), 3.58-3.60 (m, 12H, H-f, H-g, H-h), 2.45 (s, 6H, H-a); $^{13}$C NMR (100 MHz, CDCl$_3$): δ 144.6, 132.7, 129.6, 127.6, 70.4, 70.3, 70.2, 69.1, 68.3, 21.3; FT-IR (neat): 2874, 1598, 1355, 1177, 1098, 923, 664, 555 (cm$^{-1}$); HRMS (ESI-TOF) Calcd for C$_{24}$H$_{39}$N$_2$O$_7$ [M+Na]$^+$ 467.2758, found 467.2757.

Example 4-1-3

Synthesis of 10-((4-methoxybenzyl)oxy)-1-decen-3-ol

To a solution of 8-((4-methoxybenzyl)oxy)octa-1-nal (2.90 g, 11.0 mmol, 1.00 eq.) in dry tetrahydrofuran (22.0 mL), was dropwise added vinylmagnesium chloride (7.54 mL, 12.1 mmol, 1.10 eq., 1.6 M in THF solution) over 20 minutes with ice-cooling. The mixture was allowed to react for 10 minutes with ice-cooling, and then the resulting reaction solution was poured into a saturated aqueous ammonium chloride solution. The organic phase was extracted with ethyl acetate, and then the resulting organic phase was washed with a saturated aqueous ammonium chloride solution and a saturated salt solution. The washed organic phase was dried over magnesium sulfate and then concentrated under reduced pressure. The resulting residue was purified by silica gel column chromatography (elution solvent: hexane/ethyl acetate=90:10) to obtain 10-((4-methoxybenzyl)oxy)-1-decen-3-ol as shown below (2.29 g, 7.83 mmol, 71%).

[Formula 49]

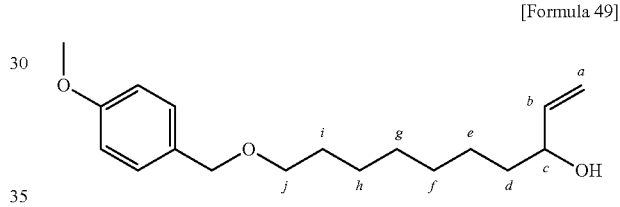

Furthermore, the analysis results of the obtained compound were as follows.

$^1$H NMR (400 MHz, CDCl$_3$): δ 7.25 (d, 2H, aromatic, J=8.2 Hz), 6.87 (d, 2H, aromatic, J=8.2 Hz), 5.86 (ddt, 1H, H-b, $J_{a,b}$=18.4 Hz, $J_{a',b}$=11.6 Hz, $J_{b,c}$=6.3 Hz), 5.21 (dd, 1H, H-a, $J_{a,b}$=18.4 Hz, $J_{a',a}$=1.5 Hz), 5.10 (dd, 1H, H-a', $J_{a',b}$=11.6 Hz, $J_{a,a}$=1.5 Hz), 4.43 (br-s, 2H, 4-MeOBn), 4.09 (q, 1H, H-c, $J_{b,c}$=$J_{c,d}$=6.3 Hz), 3.80 (s, 3H, Me), 3.43 (t, 2H, H-j, $J_{i,j}$=6.8 Hz), 1.31-1.61 (m, 12H, H-d, H-e, H-f, H-g, H-h, H-i); $^{13}$C NMR (100 MHz, CDCl$_3$): δ 158.9, 141.3, 130.6, 129.1, 114.2, 72.9, 72.3, 70.0, 55.1, 36.9, 29.5, 29.3, 29.2, 26.0, 25.1; FT-IR (neat): 2874, 1598, 1355, 1177, 1098, 923, 664, 555 (cm$^{-1}$); HRMS (ESI-TOF) Calcd for C$_{24}$H$_{39}$N$_2$O$_7$ [M+Na]$^+$ 467.2758, found 467.2757.

Example 4-1-4

Synthesis of 1-decene-3,10-diol

To an aqueous solution of 10-((4-methoxybenzyl)oxy)-1-decene-3-ol (590 mg, 2.02 mmol, 1.00 eq.) in methylene chloride (20.0 mL) and saturated sodium bicarbonate (10.0 mL), was added DDQ (687 mg, 3.03 mmol, 1.50 eq.) at room temperature. The mixture was allowed to react at the same temperature for 5 hours, and then the reaction solution was poured into 10% aqueous sodium thiosulfate solution. The organic phase was extracted with ethyl acetate, and then the resulting organic phase was washed with 10% aqueous sodium thiosulfate solution, a saturated aqueous sodium bicarbonate solution, and a saturated salt solution. The washed organic phase was dried over magnesium sulfate and then concentrated under reduced pressure. The resulting residue was purified by silica gel column chromatography (elution solvent: hexane/ethyl acetate=70:30) to obtain 1-decene-3,10-diol as shown below (324 mg, 1.88 mmol, 93%).

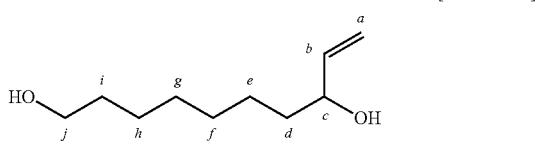

[Formula 50]

Furthermore, the analysis results of the obtained compound were as follows.

$^1$H NMR (400 MHz, CDCl$_3$): δ 5.86 (ddt, 1H, H-b, $J_{a,b}$=17.4 Hz, $J_{a',b}$=10.6 Hz, $J_{b,c}$=6.3 Hz), 5.21 (br-d, 1H, H-a, $J_{a,b}$=17.4 Hz), 5.09 (dd, 1H, H-a', $J_{a',b}$=10.6 Hz), 4.08 (q, 1H, H-c, $J_{b,c}$=$J_{c,d}$=6.3 Hz), 3.63 (t, 2H, H-j, $J_{i,j}$=6.8 Hz), 1.32-1.69 (m, 12H, H-d, H-e, H-f, H-g, H-h, H-i); $^{13}$C NMR (100 MHz, CDCl$_3$): δ 141.3, 114.5, 73.2, 63.0, 37.0, 32.7, 29.4, 29.3, 25.6, 25.2; FT-IR (neat): 2874, 1598, 1355, 1177, 1098, 923, 664, 555 (cm$^{-1}$); HRMS (ESI-TOF) Calcd for C$_{24}$H$_{39}$N$_2$O$_7$ [M+Na]$^+$ 467.2758, found 467.2757.

Example 4-1-5

Synthesis of 8-oxo-9-decenoic acid

To a solution of 1-decene-3,10-diol (920 mg, 5.34 mmol, 1.00 eq.) in 1,4-dioxane (15.0 mL) and H$_2$O (10.0 mL), were added a catalytic amount of TEMPO and phenyliodine diacetate (2.06 g, 6.41 mmol, 1.20 eq.) at room temperature. The mixture was allowed to react at the same temperature for 20 hours, and then the reaction solution was poured into 1 M aqueous hydrochloric acid solution and a saturated salt solution. The organic phase was extracted with chloroform. Then, the resulting organic phase was dried over magnesium sulfate and then concentrated under reduced pressure. The resulting residue was purified by silica gel column chromatography (elution solvent: chloroform/methanol=97:3) to obtain 8-oxo-9-decenoic acid as shown below (915 mg, 4.97 mmol, 93%).

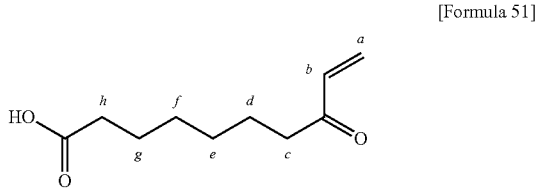

[Formula 51]

Furthermore, the analysis results of the obtained compound were as follows.

$^1$H NMR (400 MHz, CDCl$_3$): δ 6.35 (dd, 1H, H-b, $J_{a,b}$=17.4 Hz, $J_{a',b}$=10.6 Hz), 6.21 (dd, 1H, H-a, $J_{a,b}$=17.4 Hz, $J_{gem}$=1.5 Hz), 5.82 (dd, 1H, H-a', $J_{a',b}$=10.2 Hz, $J_{gem}$=1.5 Hz), 2.58 (t, 2H, H-c, $J_{e,f}$=7.3 Hz), 2.35 (t, 2H, H-h, $J_{g,h}$=7.3 Hz), 1.59-1.68 (m, 4H, H-d, H-g), 1.32-1.38 (m, 4H, H-e, H-f); $^{13}$C NMR (100 MHz, CDCl$_3$): δ 179.4, 141.1, 114.7, 73.2, 36.8, 34.0, 29.1, 28.9, 25.0, 24.6; FT-IR (neat): 2874, 1598, 1355, 1177, 1098, 923, 664, 555 (cm$^{-1}$); HRMS (ESI-TOF) Calcd for C$_{24}$H$_{39}$N$_2$O$_7$ [M+Na]$^+$ 467.2758, found 467.2757.

Example 4-1-6

Synthesis of 8-hydroxy-9-decenoic acid

To a solution of 8-oxo-9-decenoic acid (910 mg, 4.94 mmol, 1.00 eq.) in MeOH (20.0 mL), was added CeCl$_3$.7H$_2$O (2.76 g, 7.41 mmol, 1.50 eq.). The mixture was stirred for 30 minutes with ice-cooling, and then thereto was slowly added sodium borohydride (224 mg, 5.93 mmol, 1.20 eq.). The mixture was stirred for 1 hour, and then the reaction solution was poured into 1 M aqueous hydrochloric acid solution. The organic phase was extracted with chloroform. Then, the resulting organic phase was dried over magnesium sulfate and concentrated under reduced pressure. The resulting residue was purified by silica gel column chromatography (elution solvent: chloroform/methanol=97:3) to obtain 8-hydroxy-9-decenoic acid as shown below (870 mg, 4.55 mmol, 92%).

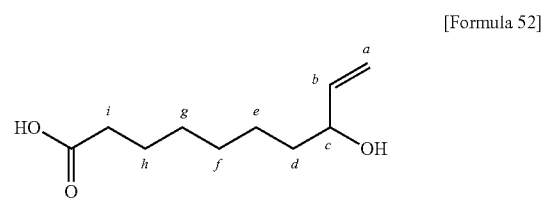

[Formula 52]

Furthermore, the analysis results of the obtained compound were as follows.

$^1$H NMR (400 MHz, CDCl$_3$): δ 5.83 (ddt, 1H, H-b, $J_{a,b}$=17.4 Hz, $J_{a',b}$=10.2 Hz, $J_{b,c}$=6.8 Hz), 5.20 (br-d, 1H, H-a, $J_{a,b}$=17.4 Hz), 5.09 (br-d, 1H, H-a', $J_{a',b}$=10.2 Hz), 4.09 (q, 1H, H-c, $J_{b,c}$=$J_{c,d}$=6.8 Hz), 2.33 (t, 2H, H-i, $J_{h,i}$=7.3 Hz), 1.33-1.64 (m, 12H, H-d, H-e, H-f, H-g, H-h); $^{13}$C NMR (100 MHz, CDCl$_3$): δ 179.4, 141.1, 114.7, 73.2, 36.8, 34.0, 29.1, 28.9, 25.0, 24.6; FT-IR (neat): 2874, 1598, 1355, 1177, 1098, 923, 664, 555 (cm$^{-1}$); HRMS (ESI-TOF) Calcd for C$_{24}$H$_{39}$N$_2$O$_7$[M+Na]$^+$ 467.2758, found 467.2757.

Example 4-2

Synthesis of Solid Phase-Supported Allyl TFA Ester

The synthesis steps of solid phase-supported allyl TFA ester are shown below.

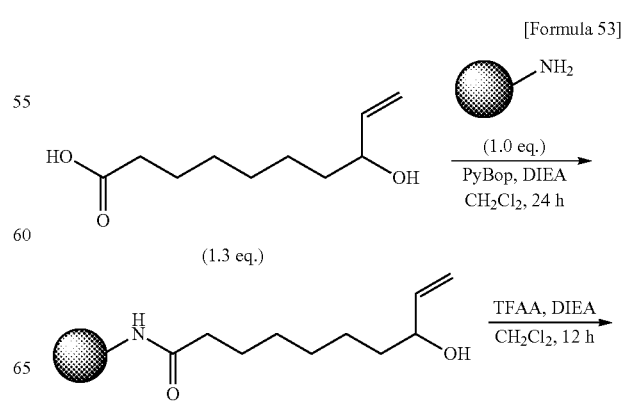

[Formula 53]

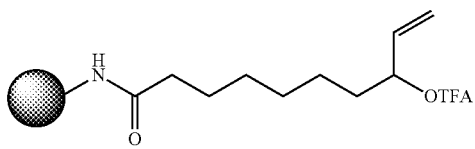

Example 4-2-1

Synthesis of Solid Phase-Supported Allyl Alcohol

To a solution of 8-hydroxy-9-decenoic acid (50.0 mg, 0.268 mmol, 1.30 eq.) in dry methylene chloride (2.10 mL), were added TentaGel-$NH_2$ resin (480 mg, 0.207 mmol, 1.00 eq., 0.43 mmol/g), PyBop (215 mg, 0.413 mmol, 2.00 eq.) and DIEA (103 µL, 0.620 mmol, 3.00 eq.) at room temperature. The mixture was stirred for 24 hours at room temperature and filtered to remove the solid phase. The obtained solid phase was washed with THF/$H_2O$ (1/1) (1.00 mL), MeOH (1.00 mL), and dry $CH_2Cl_2$ (1.00 mL) to obtain the solid phase-supported allyl alcohol as shown below.

[Formula 54]

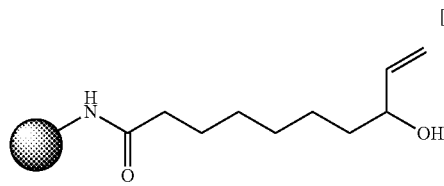

Furthermore, the analysis result of the obtained compound was as follows.
FT-IR (neat): 2927, 1653, 1452, 1117, 700, 551 ($cm^{-1}$).

Example 4-2-2

Synthesis of Solid Phase-Supported Allyl TFA Ester

Subsequently, the solid phase-supported allyl alcohol was put into dry methylene chloride (2.00 mL), and thereto were added trifluoroacetic anhydride (287 µL, 2.07 mmol, 20.0 eq.) and diisopropylethylamine (890 µL, 5.16 mmol, 50.0 eq.). The mixture was allowed to react at room temperature for 12 hours, and then the solid phase was removed, washed with methylene chloride, and dried under reduced pressure to thereby obtain a solid phase-supported allyl TFA ester as shown below.

[Formula 55]

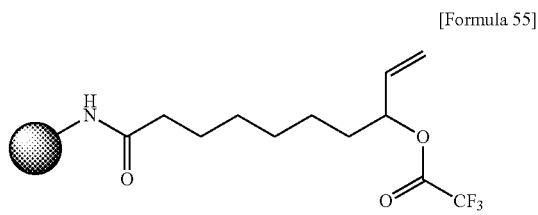 [SMILES: C=CC(CCCCCCC(=O)NC)OC(=O)C(F)(F)F]

Furthermore, the analysis result of the obtained compound was as follows.
FT-IR (neat): 2928, 1782, 1671, 1452, 1140, 704,531 ($cm^{-1}$).

Example 4-3

Synthesis of Solid Phase-Supported Copolymer

The synthesis steps of a solid phase-supported copolymer are shown below.

[Formula 56]

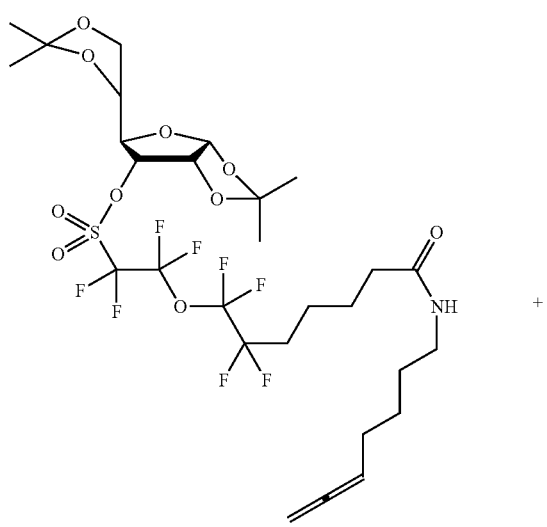

(1.0 eq.)

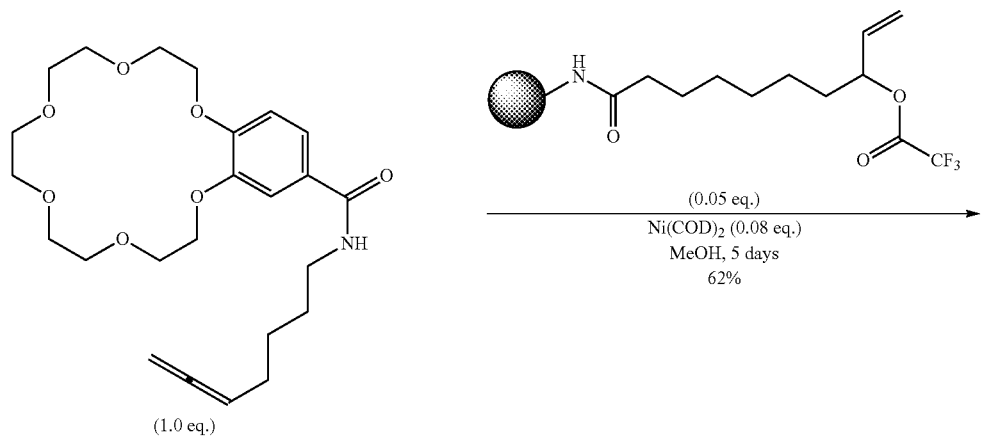

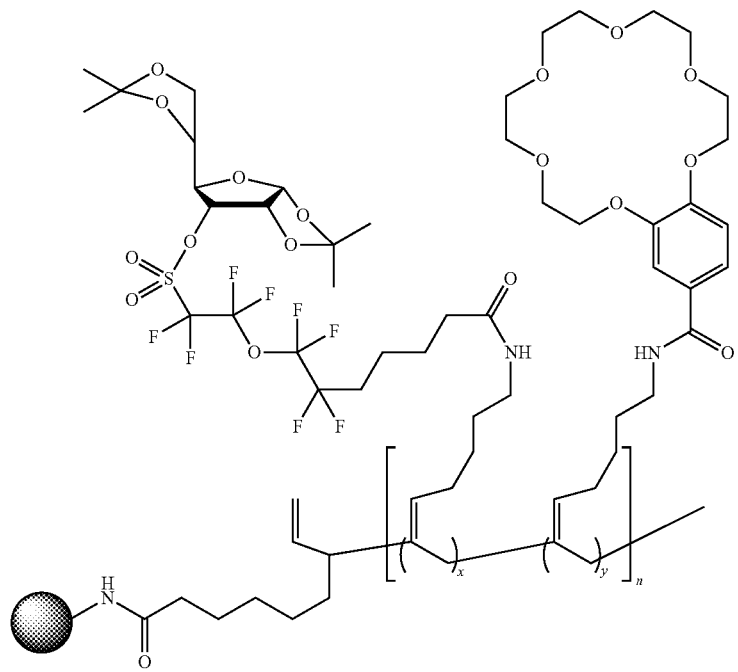

The solid phase-supported allyl TFA ester (45.0 mg, 19.4 μmol, 0.0500 eq.) was allowed to react with a solution of 0.1M Ni(COD)$_2$ in toluene (310 μL, 31.0 μmol, 0.0800 eq.) in a nitrogen atmosphere. They were allowed to react with each other for 20 minutes, and then excess Ni(COD)$_2$ solution was removed. Thereto was added a solution of a 3-FDG monomer (284 mg, 387 μmol, 1.00 eq.) and a crown ether monomer (174 mg, 387 μmol, 1.00 eq.) in MeOH (500 μL) at room temperature, and the resulting mixture was allowed to react for 5 days to obtain a solid phase-supported copolymer as shown below (319 mg, 62%).

[Formula 57]
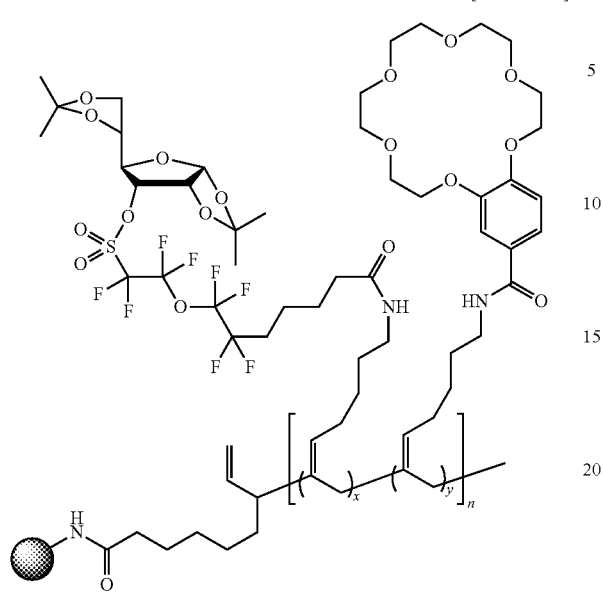
Furthermore, the analysis result of the obtained compound was as follows.
FT-IR (neat): 3284, 2930, 1640, 1507, 1264, 1121, 959, 770 (cm$^{-1}$).
Example 4-4
Removal of 3-FDG
Example 4-4-1
Removal with TBAI
The removing steps with TBAI are shown below.
[Formula 58]
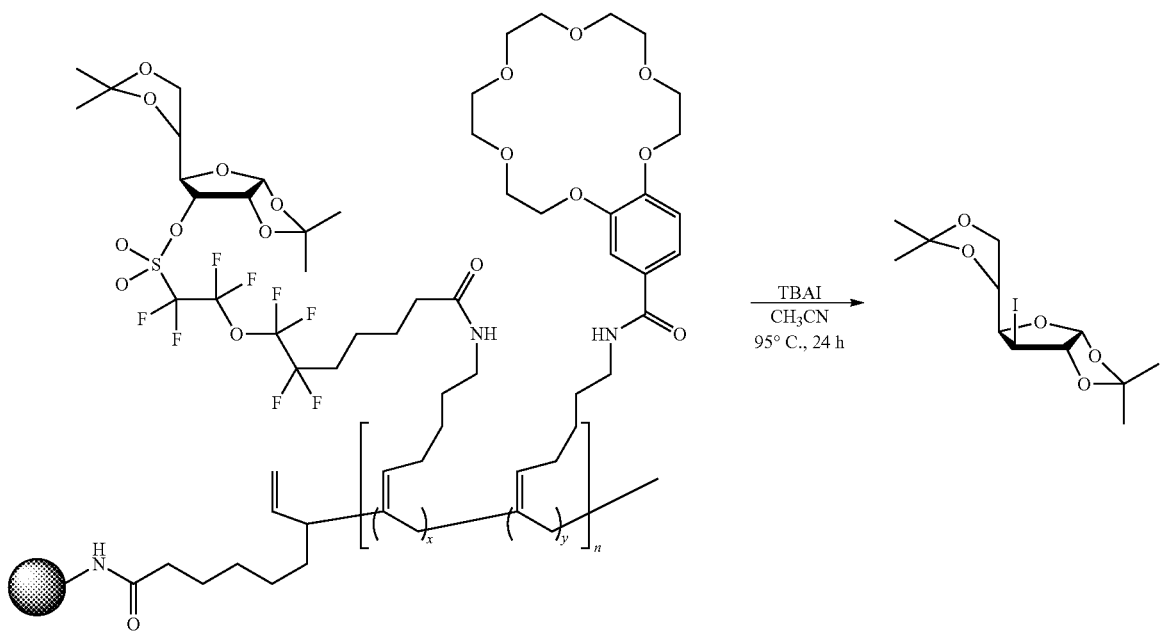

To a solution of the solid phase-supported copolymer (29.1 mg) in acetonitrile CH$_3$CN (1.00 mL) was added tetrabutylammonium iodide (110 mg) at room temperature. They were allowed to react with each other at 95 degrees for 24 hours to obtain 3-deoxy-3-iodo-1,2,5,6-di-O-isopropylidene-α-D-glucofuranose as shown below. The quantitative analysis of this compound revealed that a 3-FDG precursor in an amount of 0.371 mmol/g was immobilized in the solid phase-supported copolymer.

[Formula 60]

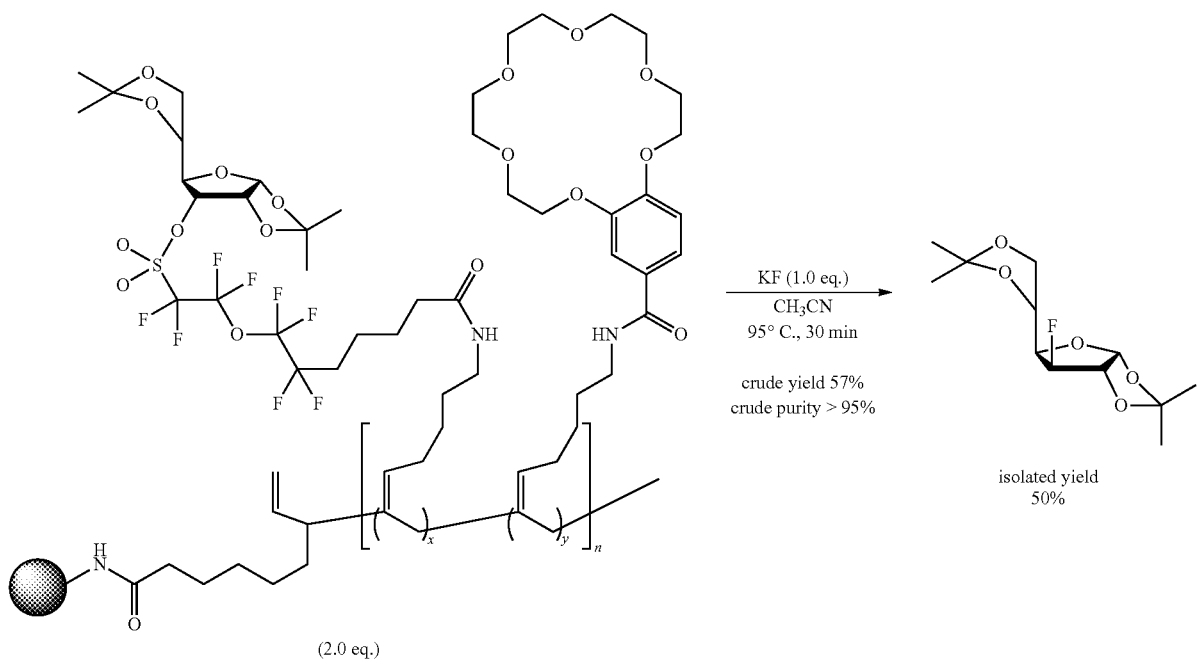

[Formula 59]

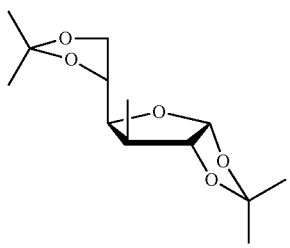

Furthermore, the analysis results of the obtained compound were as follows.

$[α]_D^{26}$ −20.8 (c 0.900, CHCl$_3$); $^1$H NMR (400 MHz, CDCl$_3$): δ 5.98 (d, 1H, H-1, $J_{1,2}$=3.4 Hz), 5.06 (d, 1H, H-3, $J_{3,4}$=3.4 Hz), 4.56 (d, 1H, H-2, $J_{1,2}$=3.4 Hz), 4.04-4.16 (m, 3H, H-5, H-6a, H-6b), 3.28 (dd, 1H, H-4, $J_{3,4}$=3.4 Hz, $J_{4,5}$=7.3 Hz), 4.10 (ddd, 1H, H-4, $J_{3,4}$=4.8 Hz, $J_{4,5}$=7.7 Hz, $J_{4,F}$=27.4 Hz), 4.02 (dd, 1H, H-6b, $J_{5,6b}$=6.3 Hz, $J_{6a,6b}$=8.7 Hz), 1.51 (s, 3H, CH$_3$), 1.42 (s, 3H, CH$_3$), 1.36 (s, 3H, CH$_3$), 1.32 (s, 3H, CH$_3$); $^{13}$C NMR (100 MHz, CDCl$_3$): δ (112.7, 109.6, 104.9 anomeric, isopropylidene), 88.4, 79.7, 79.1, 67.4, 34.1, 27.0, 26.6, 26.4, 25.1; FT-IR (neat): 2987, 1373, 1212, 1065, 845 (cm$^{-1}$); HRMS (ESI-TOF) Calcd for C$_{12}$H$_{20}$O$_5$F [M+H]$^+$ 263.1292, found 262.1295.

Example 4-4-2

Removal with KF

The removing steps with KF are shown below.

To a solution of the solid phase-supported copolymer (54.5 mg, 20.2 μmol, 2.00 eq.) in CH$_3$CN (220 μL) was added KF (10.0 μL, 10.1 μmol, 1.00 eq., 1.0 M in H$_2$O solution) at room temperature. The mixture was allowed to react at 95 degrees for 30 minutes. The solid phase was removed by filtration. Further, the solid phase was washed with acetonitrile (1.00 mL). The filtrate was concentrated under reduced pressure and purified by column chromatography to thereby obtain 3-deoxy-3-fluoro-1,2,5,6-di-O-isopropylidene-α-D-glucofuranose (1.30 mg, 5.00 μmol, 50%).

Industrial Applicability

The present invention enables efficient production of an $^{18}$F-labeled compound. The $^{18}$F-labeled compound is useful as a probe for PET used for the diagnosis of various diseases. Therefore, the present invention is available in the fields of industry such as pharmaceuticals.

The present specification includes the contents described in the specification and/or drawings of Japanese Patent Application (No. 2010-029295) which is the basis of the priority of the present application. Furthermore, all the publications, patents, and patent applications cited in the present specification are incorporated into the present specification by reference in their entirety.

The invention claimed is:

1. A method for producing an $^{18}$F-labeled compound, comprising:
   contacting a high molecular compound with $^{18}$F$^-$, wherein covalently attached to the high molecular compound are both a precursor compound to be labeled and a phase transfer catalyst, thereby labeling the precursor compound with $^{18}$F; and
   separating the $^{18}$F labeled compound from the high molecular compound.

2. The method for producing an $^{18}$F-labeled compound according to claim 1, wherein the high molecular compound is a high molecular compound obtained by copolymerization of a monomer comprising a residue of a precursor compound to be labeled and a monomer comprising a residue of a phase transfer catalyst.

3. The method for producing an $^{18}$F-labeled compound according to claim 2, wherein the monomer comprising the residue of the precursor compound to be labeled is represented by the following formula (I):

$$CH_2=C=CH-L^1-SO_2-X \quad (I)$$

wherein $L^1$ represents a linker, and X represents the residue of the precursor compound to be labeled; and the monomer comprising the residue of the phase transfer catalyst is represented by the following formula (II):

$$CH_2=C=CH-L^2-Y \quad (II)$$

wherein $L^2$ represents a linker, and Y represents the residue of the phase transfer catalyst.

4. The method for producing an $^{18}$F-labeled compound according to any one of claims 1 to 3, wherein the high molecular compound comprises structural units represented by formulas (Ia), (Ib), (IIa), and (IIb):

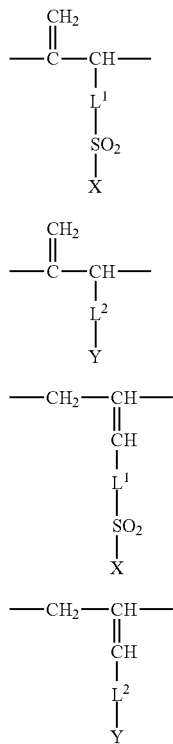

wherein $L^1$ and $L^2$ each represents a linker; X represents the residue of the precursor compound to be labeled; and Y represents the residue of the phase transfer catalyst.

5. The method for producing an $^{18}$F-labeled compound according to claim 1, wherein the phase transfer catalyst is 1,10-diaza-4,7,13,16,21,24-hexaoxabicyclo[8.8.8]hexacosane, 12-crown-4, 15-crown-5, 18-crown-6, benzo-12-crown-4, benzo-15-crown-5, or benzo-18-crown-6.

6. The method for producing an $^{18}$F-labeled compound according to claim 1, wherein the precursor compound to be labeled is represented by formula (A) or (B):

wherein $R^1$, $R^2$, and $R^3$ each represents any group.

7. The method for producing an $^{18}$F-labeled compound according to claim 1, wherein the $^{18}$F-labeled compound is 2-$^{18}$F-fluoro-2-deoxy-D-glucose, 2-$^{18}$F-fluoro-2-deoxy-D-mannose, 3-$^{18}$F-fluoro-3-deoxy-D-glucose, O-(2-[$^{18}$F]fluoroethyl)-L-tyrosine, 3'-[$^{18}$F]-fluoro-3'-deoxythymidine, 16α-[$^{18}$F]-fluoro-17β-estradiol, or [$^{18}$F]-fluoromisonidazole.

8. A high molecular compound comprising structural units represented by the following formulas (Ia), (Ib), (IIa), and (IIb):

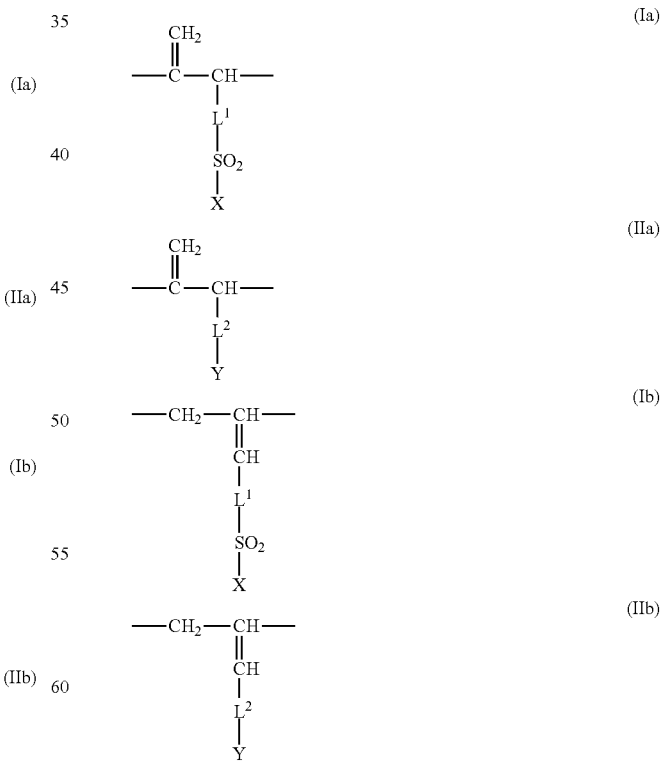

wherein $L^1$ and $L^2$ each represents a linker; X represents a residue of a precursor compound to be labeled with $^{18}$F; and Y represents a residue of a phase transfer catalyst.

9. The high molecular compound according to claim 8, wherein the phase transfer catalyst is 1,10-diaza-4,7,13,16,21,24-hexaoxabicyclo[8.8.8]hexacosane, 12-crown-4, 15-crown-5, 18-crown-6, benzo-12-crown-4, benzo-15-crown-5, or benzo-18-crown-6.
10. The high molecular compound according to claim 8 or 9, wherein the precursor compound to be labeled is represented by formula (A) or (B):
wherein $R^1$, $R^2$, and $R^3$ each represents any group.
* * * * *